United States Patent
Matsiev et al.

(10) Patent No.: US 7,350,367 B2
(45) Date of Patent: Apr. 1, 2008

(54) ENVIRONMENTAL CONTROL SYSTEM FLUID SENSING SYSTEM AND METHOD

(75) Inventors: Leonid Matsiev, San Jose, CA (US); Oleg Kolosov, San Jose, CA (US); Mark D. Uhrich, Redwood City, CA (US); William Rust, Mountain View, CA (US); John M. Feland, III, Palo Alto, CA (US); John F. Varni, Los Gatos, CA (US); Blake Walker, Pleasanton, CA (US)

(73) Assignee: Visyx Technologies, Inc., Santa Clara, CA (US)

( * ) Notice: Subject to any disclaimer, the term of this patent is extended or adjusted under 35 U.S.C. 154(b) by 212 days.

(21) Appl. No.: 10/951,252

(22) Filed: Sep. 27, 2004

(65) Prior Publication Data

US 2005/0145019 A1    Jul. 7, 2005

Related U.S. Application Data

(60) Provisional application No. 60/505,943, filed on Sep. 25, 2003.

(51) Int. Cl.
*F25B 49/00* (2006.01)
*F25B 41/04* (2006.01)
*G01N 29/02* (2006.01)

(52) U.S. Cl. .......................... 62/129; 62/225; 73/24.01; 73/54.41

(58) Field of Classification Search .................. 62/125, 62/126, 129, 131, 225; 73/10, 53.01, 24.01, 73/24.04, 24.06, 54.41; 702/50
See application file for complete search history.

(56) References Cited

U.S. PATENT DOCUMENTS 3,273,377 A    9/1966 Testerman et al.

(Continued)

FOREIGN PATENT DOCUMENTS

DE    4424422    1/1996

(Continued)

OTHER PUBLICATIONS

Fisch, M.R., et al., "Improved Acoustic Viscosimeter Technique", J. Acoust. Soc. Am., Sep. 1976, pp. 623-625, v. 60, No. 3.

(Continued)

*Primary Examiner*—Marc Norman
(74) *Attorney, Agent, or Firm*—Senniger Powers

(57) ABSTRACT

A system for monitoring a fluid in an environmental control system includes a mechanical resonator positioned for contacting a thermal change fluid. In some embodiments, the mechanical resonator is positioned in a passage for containing the thermal change fluid. Suitable thermal change fluids include an R-134A refrigerant, a mineral oil, an ester lubricant or a mixture thereof; a superheated refrigerant; or an elevated pressure and elevated temperature vapor, an elevated pressure liquid, a reduced pressure liquid, a reduced pressure vapor and combinations thereof. The mechanical resonator can be a flexural resonator or a torsion resonator. In some embodiments, the mechanical resonator is a tuning fork resonator. Methods of the invention include monitoring a response of the mechanical resonator to the thermal change fluid. In some embodiments, at least a portion of the mechanical resonator is translated through the thermal change fluid and the response of the resonator to the fluid is monitored.

43 Claims, 7 Drawing Sheets

U.S. PATENT DOCUMENTS

| | | |
|---|---|---|
| 3,622,968 A | 11/1971 | Silverman |
| 3,710,275 A | 1/1973 | Tanaka et al. |
| 3,718,032 A | 2/1973 | Gray |
| 3,762,197 A | 10/1973 | Roof et al. |
| 3,778,757 A | 12/1973 | Houston |
| 3,902,365 A | 9/1975 | Knauth |
| 3,903,732 A | 9/1975 | Rork et al. |
| 3,921,622 A | 11/1975 | Cole |
| 3,926,271 A | 12/1975 | Patashnick |
| 4,103,224 A | 7/1978 | Taro et al. |
| 4,145,922 A | 3/1979 | Estrada, Jr. et al. |
| 4,312,228 A | 1/1982 | Wohltjen |
| 4,342,936 A | 8/1982 | Marcus et al. |
| 4,349,881 A | 9/1982 | November et al. |
| 4,361,026 A | 11/1982 | Muller et al. |
| 4,370,662 A | 1/1983 | Hou et al. |
| 4,391,338 A | 7/1983 | Patashnick et al. |
| 4,526,480 A | 7/1985 | Ward |
| 4,535,620 A | 8/1985 | Cunnungham |
| 4,543,829 A | 10/1985 | Lerch |
| 4,549,427 A | 10/1985 | Kolesar, Jr. |
| 4,596,697 A | 6/1986 | Ballato |
| 4,602,505 A | 7/1986 | Kanda et al. |
| 4,624,129 A | 11/1986 | Haynes |
| 4,644,803 A | 2/1987 | Ward |
| 4,696,181 A | 9/1987 | Rupprecht et al. |
| 4,721,874 A | 1/1988 | Emmert |
| 4,729,237 A | 3/1988 | Suzuki et al. |
| 4,734,609 A | 3/1988 | Jasmine |
| 4,741,200 A | 5/1988 | Hammerle |
| 4,760,351 A | 7/1988 | Newell et al. |
| 4,767,719 A | 8/1988 | Finlan |
| 4,779,451 A | 10/1988 | Ezawa et al. |
| 4,782,332 A | 11/1988 | Cipris et al. |
| 4,783,987 A | 11/1988 | Hager et al. |
| 4,802,370 A | 2/1989 | EerNisse et al. |
| 4,802,384 A | 2/1989 | Schwarz et al. |
| 4,812,698 A | 3/1989 | Chida et al. |
| 4,862,384 A | 8/1989 | Bujard |
| 4,890,480 A | 1/1990 | Young |
| 4,893,496 A | 1/1990 | Bau et al. |
| 4,904,978 A | 2/1990 | Barth et al. |
| 4,910,523 A | 3/1990 | Huguenin et al. |
| 4,922,745 A | 5/1990 | Rudkin et al. |
| 4,970,492 A | 11/1990 | King |
| 5,006,845 A | 4/1991 | Calcar et al. |
| 5,179,028 A | 1/1993 | Valie et al. |
| 5,191,791 A | 3/1993 | Gerardi et al. |
| 5,201,215 A | 4/1993 | Granstaff et al. |
| 5,204,529 A | 4/1993 | Diatschenko |
| 5,224,174 A | 6/1993 | Schneider et al. |
| 5,235,844 A | 8/1993 | Bonne et al. |
| 5,253,530 A | 10/1993 | Letcher, III |
| 5,283,037 A | 2/1994 | Baer et al. |
| 5,296,374 A | 3/1994 | Culshaw et al. |
| 5,306,644 A | 4/1994 | Myerholtz et al. |
| 5,325,704 A | 7/1994 | Mariami et al. |
| 5,332,961 A | 7/1994 | Hammerle |
| 5,334,900 A | 8/1994 | Kawashima |
| 5,338,416 A | 8/1994 | Mlcak et al. |
| 5,357,964 A | 10/1994 | Spivey et al. |
| 5,361,632 A | 11/1994 | Magnani |
| 5,375,470 A | 12/1994 | Matsushima et al. |
| 5,421,190 A | 6/1995 | Brandle et al. |
| 5,434,650 A | 7/1995 | Nakahara et al. |
| 5,435,170 A | 7/1995 | Voelker et al. |
| 5,445,008 A | 8/1995 | Wachter et al. |
| 5,454,045 A | 9/1995 | Perkins et al. |
| 5,455,475 A | 10/1995 | Josse et al. |
| 5,464,509 A | 11/1995 | Mlcak et al. |
| 5,469,369 A | 11/1995 | Rose-Pehrsson et al. |
| 5,477,726 A | 12/1995 | Stabinger et al. |
| 5,488,866 A | 2/1996 | Ravel et al. |
| 5,524,477 A | 6/1996 | Wajid |
| 5,524,636 A | 6/1996 | Sarvazyan et al. |
| 5,531,091 A | 7/1996 | Gademann et al. |
| 5,533,402 A | 7/1996 | Sarvazyan et al. |
| 5,571,401 A | 11/1996 | Lewis et al. |
| 5,571,952 A | 11/1996 | Kauzlarich |
| 5,604,441 A | 2/1997 | Freese, V et al. |
| 5,622,223 A | 4/1997 | Vasquez |
| 5,653,939 A | 8/1997 | Hollis et al. |
| 5,661,233 A | 8/1997 | Spates et al. |
| 5,670,709 A | 9/1997 | Gallagher |
| 5,698,089 A | 12/1997 | Lewis et al. |
| 5,705,399 A | 1/1998 | Larue |
| 5,734,098 A | 3/1998 | Kraus et al. |
| 5,741,961 A | 4/1998 | Martin et al. |
| 5,741,962 A | 4/1998 | Birchak et al. |
| 5,744,902 A | 4/1998 | Vig |
| 5,770,038 A | 6/1998 | Iwama et al. |
| 5,776,359 A | 7/1998 | Schultz et al. |
| 5,777,210 A | 7/1998 | Voelker et al. |
| 5,789,665 A | 8/1998 | Voelker et al. |
| 5,792,938 A | 8/1998 | Gokhfeld |
| 5,798,452 A | 8/1998 | Martin et al. |
| 5,818,731 A | 10/1998 | Mittal et al. |
| 5,827,952 A | 10/1998 | Mansure et al. |
| 5,852,229 A | 12/1998 | Josse et al. |
| 5,885,849 A | 3/1999 | Di Stefano et al. |
| 5,889,351 A | 3/1999 | Okumura et al. |
| 5,915,499 A | 6/1999 | Few |
| 5,918,354 A | 7/1999 | Ikegami et al. |
| 5,959,297 A | 9/1999 | Weinberg et al. |
| 5,985,356 A | 11/1999 | Schultz et al. |
| 6,023,961 A | 2/2000 | Discenzo et al. |
| 6,034,775 A | 3/2000 | McFarland et al. |
| 6,041,642 A | 3/2000 | Duncan |
| 6,044,694 A | 4/2000 | Anderson et al. |
| 6,126,311 A | 10/2000 | Schuh |
| 6,151,123 A | 11/2000 | Nielsen |
| 6,155,098 A | 12/2000 | Shapiro et al. |
| 6,157,449 A | 12/2000 | Hajduk |
| 6,175,409 B1 | 1/2001 | Nielsen et al. |
| 6,176,323 B1 | 1/2001 | Weirich et al. |
| 6,182,499 B1 | 2/2001 | McFarland et al. |
| 6,223,589 B1 | 5/2001 | Dickert et al. |
| 6,247,354 B1 | 6/2001 | Vig et al. |
| 6,260,407 B1 | 7/2001 | Petro et al. |
| 6,260,408 B1 | 7/2001 | Vig et al. |
| 6,265,226 B1 | 7/2001 | Petro et al. |
| 6,269,686 B1 | 8/2001 | Hahn et al. |
| 6,275,137 B1 | 8/2001 | Doppalapudi et al. |
| 6,286,363 B1 | 9/2001 | Discenzo |
| 6,294,388 B1 | 9/2001 | Petro et al. |
| 6,296,771 B1 | 10/2001 | Miroslav |
| 6,306,358 B1 | 10/2001 | Yamamoto |
| 6,311,549 B1 | 11/2001 | Thundat et al. |
| 6,327,890 B1 | 12/2001 | Galipeau et al. |
| 6,336,353 B2 | 1/2002 | Matsiev et al. |
| 6,371,640 B1 | 4/2002 | Hajduk |
| 6,393,895 B1 | 5/2002 | Matsiev et al. |
| 6,401,519 B1 | 6/2002 | McFarland et al. |
| 6,407,479 B1 | 6/2002 | Moellendorf et al. |
| 6,412,131 B1 | 7/2002 | Zhao et al. |
| 6,441,716 B1 | 8/2002 | Doppalapudi et al. |
| 6,456,096 B1 | 9/2002 | Ericson et al. |
| 6,459,995 B1 | 10/2002 | Collister |
| 6,494,079 B1 | 12/2002 | Matsiev et al. |
| 6,509,749 B1 | 1/2003 | Buelna et al. |
| 6,511,915 B2 | 1/2003 | Mlcak |
| 6,519,034 B1 | 2/2003 | Engler et al. |
| 6,535,001 B1 | 3/2003 | Wang |
| 6,536,634 B2 | 3/2003 | Berndorfer et al. |

| | | | | | | |
|---|---|---|---|---|---|---|
| 6,545,392 | B2 | 4/2003 | Kawauchi et al. | WO | WO 02/077613 | 10/2002 |
| 6,557,396 | B2 | 5/2003 | Ismail et al. | WO | WO 03/014732 | 2/2003 |
| 6,564,126 | B1 | 5/2003 | Lin et al. | WO | WO 03/100390 | 4/2003 |
| 6,626,025 | B2 | 9/2003 | Potyrailo et al. | WO | WO 03/054482 | 7/2003 |
| 6,640,644 | B1 | 11/2003 | Mireles et al. | WO | WO 2004/036191 | 4/2004 |
| 6,644,095 | B2 | 11/2003 | Van Mullekom et al. | | | |
| 6,661,162 | B1 | 12/2003 | Nagai et al. | | | |
| 6,925,822 | B2 | 8/2005 | Lifson et al. | | | |
| 7,043,969 | B2 * | 5/2006 | Matsiev et al. ............ 73/54.41 | | | |
| 2001/0010174 | A1 | 8/2001 | Matsiev et al. | | | |
| 2002/0064649 | A1 | 5/2002 | Lembke et al. | | | |
| 2002/0068488 | A1 | 6/2002 | Tuller et al. | | | |
| 2002/0070841 | A1 | 6/2002 | Doppalapudi et al. | | | |
| 2002/0074897 | A1 | 6/2002 | Ma et al. | | | |
| 2002/0092340 | A1 | 7/2002 | Prater et al. | | | |
| 2002/0113596 | A1 | 8/2002 | Horie et al. | | | |
| 2002/0121132 | A1 | 9/2002 | Breed et al. | | | |
| 2002/0137348 | A1 | 9/2002 | Mlcak | | | |
| 2002/0148529 | A1 | 10/2002 | Berndorfer et al. | | | |
| 2002/0162385 | A1 | 11/2002 | Ismail et al. | | | |
| 2002/0162390 | A1 | 11/2002 | Ismail et al. | | | |
| 2002/0178787 | A1 | 12/2002 | Matsiev et al. | | | |
| 2002/0178805 | A1 | 12/2002 | DiFoggio et al. | | | |
| 2002/0194906 | A1 | 12/2002 | Goodwin et al. | | | |
| 2003/0000291 | A1 | 1/2003 | Kolosov et al. | | | |
| 2003/0041653 | A1 | 3/2003 | Matsiev et al. | | | |
| 2003/0041659 | A1 | 3/2003 | Marszalek et al. | | | |
| 2003/0062910 | A1 | 4/2003 | Wang et al. | | | |
| 2003/0083825 | A1 | 5/2003 | Berndorfer | | | |
| 2003/0116497 | A1 | 6/2003 | Carlson et al. | | | |
| 2003/0118078 | A1 | 6/2003 | Carlson et al. | | | |
| 2003/0119060 | A1 | 6/2003 | Desrosiers et al. | | | |
| 2003/0124028 | A1 | 7/2003 | Carlson et al. | | | |
| 2003/0145647 | A1 | 8/2003 | Ismail et al. | | | |
| 2003/0179002 | A1 | 9/2003 | Beylich et al. | | | |
| 2003/0213292 | A1 | 11/2003 | Budeiri et al. | | | |
| 2003/0222656 | A1 | 12/2003 | Phillips et al. | | | |
| 2005/0209796 | A1 * | 9/2005 | Kolosov et al. ............ 702/52 | | | |
| 2006/0031030 | A1 * | 2/2006 | Bennett et al. ............ 702/50 | | | |

FOREIGN PATENT DOCUMENTS

| | | |
|---|---|---|
| DE | 100 14 724 | 9/2001 |
| EP | 0102490 | 3/1984 |
| EP | 0 282 251 B1 | 3/1988 |
| EP | 0 282 251 B2 | 3/1988 |
| EP | 0282251 | 9/1988 |
| EP | 0317356 B1 | 5/1989 |
| EP | 0676638 | 10/1995 |
| EP | 0 769 695 A | 4/1997 |
| EP | 0 779 510 | 6/1997 |
| EP | 0813236 | 12/1997 |
| GB | 1385488 | 8/1971 |
| GB | 2114745 | 8/1983 |
| GB | 2187286 | 9/1987 |
| JP | 59126931 | 7/1984 |
| JP | 60134617 | 7/1985 |
| JP | 5129874 | 5/1993 |
| JP | 8112613 | 5/1996 |
| JP | 11094726 | 9/1997 |
| WO | WO 91/02975 | 3/1991 |
| WO | WO 95/13278 | 5/1995 |
| WO | WO 98/01739 | 6/1997 |
| WO | WO 98/15501 | 4/1998 |
| WO | WO 98/37412 | 8/1998 |
| WO | WO 99/18431 | 4/1999 |
| WO | WO 99/51980 | 10/1999 |
| WO | WO 00/58709 | 3/2000 |
| WO | WO 00/67086 | 11/2000 |
| WO | WO 01/77624 | 10/2001 |
| WO | WO 02/12265 | 2/2002 |
| WO | WO 02/16888 | 2/2002 |
| WO | WO 02/23134 | 3/2002 |

OTHER PUBLICATIONS

Hlavay, J. and G.G. Guilbault, "Applications of the Piezoelectric Crystal Detector in Analytical Chemistry", Analytical Chemistry, Nov. 1977, pp. 1890-1898, v. 49, No. 13.

Kanazawa, K. Keiji and Joseph G. Gordon II, "The Oscillation Frequency of a Quartz Resonator in Contact with a Liquid", Analytica Chimica Acta, 1985, pp. 99-105, Elsevier Science Publishers B.V., Amsterdam.

Kipling, Arlin L and Michael Thompson, "Network Analysis Method Applied to Liquid-Phase Acoustic Wave Sensors", Anal. Chem., 1990, pp. 1514-1519, 62.

Michels, A. et al., "1 MHz Quartz Length Extension Resonator as a Probe for Scanning Near-Field Acoustic Microscopy", Thin Solid Films, 1995, pp. 172-175, 264.

Muramatsu, Hiroshi et al., "Computation of Equivalent Circuit Parameters of Quartz Crystals in Contact with Liquids and Study of Liquid Properties", Anal. Chem., 1988, pp. 2142-2146. 60.

Muramatsu, H. et al., "A Quartz Crystal Viscosity Sensor for Monitoring Coagulation Reaction and Its Application to a Multichannel Coagulation Detector", Biosensors & Bioelectronics, 1991, pp. 353-358, 6, Elsevier Science Publishers Ltd. England.

Nomura, T. and M Iijima, "Electrolytic Determination of Nanomolar Concentrations of Silver in Solution with Piezoelectric Quartz Crystal", Analytica Chimica Acta, 1981, pp. 97-102, 131, Elsevier Scientific Publishing Company.

PCT International Search Report, dated Apr. 27, 1998, PCT/US97/18192.

Newsam, J. et al., "High Throughput Experimentation for the Synthesis of New Crystalline Microporous Solids," Microporous and Mesoporous Materials 48 (2001) 355-365.

Akporiaye, D. et al., "Combinatorial Chemistry—The Emperor's New Clothes?," Microporous and Mesoporous Materials 48 (2001) 367-373.

Patent Abstracts of Japan, Publication No. 05-129874, Application No. 03-291660, filing date Nov. 7, 1991, Applicant: Seiko Epson Corp.

Abstract of Patent No. JP60134617, published Jul. 17, 1985, Applicant: Kinseki KK.

Wullner et al., Multi-Function Microsensor for Oil Condition Monitoring Systems, pp. 1-5.

Hauptmann et al., Ultrasonic Sensors for Process Monitoring and Chemical Analysis; State-of-the-Art and Trends, 1998, pp. 32-48.

Jakoby et al., Viscosity Sensing Using a Love-wave Device, 1998, pp. 275-281.

Polla et al., Processing and Characterization of Piezoelectric Materials and Integration into Microelectromechanical Systems, 1998, pp. 563-597.

Pujari et al., Reliable Ceramics for Advanced Heat Engines, American Ceramic Society Bulletin, vol. 74, No. 4, Apr. 1995, pp. 86-90.

Oden et al., Viscous Drag Measurements Utilizing Microfabricated Cantilevers, American Institute of Physics, 1996, pp. 3814-3816.

Merhaut, Theory of Electroacoustics, pp. 100 and 101.

Manalis et al., Two-dimensional Micromechanical Bimorph Arrays for Detection of Thermal Radiation, Appl. Phys. Lett., vol. 70, No. 24, Jun. 16, 1997, pp. 3311-3313.

Lin et al., Operation of an Ultrasensitive 30-MHz Quartz Crystal Microbalance in Liquids, Analytical Chemistry, Vo. 65, No. 11, Jun. 1, 1993, pp. 1546-1551.

Li et al., Electromechanical Behavior of PZT-Brass Unimorphs, Journal of the American Ceramic Society, vol. 82, No. 7, 1999, pp. 1733-1740.

Landau et al., Fluid Mechanics, pp. 96 and 97.

Cleland et al., Fabrication of High Frequency Nonometer Scale Mechanical Resonators from Bulk Si Crystals, Appl. Phys. Lett., vol. 69, No. 18, Oct. 28, 1996, pp. 2653-2655.

International Search Report mailed Jul. 9, 2004, PCT/US2004/008531 (1012.188WO1).
Ferry, Viscoelastic Properties of Polymers, Chapter 5-8, pp. 96-176.
J.W. Grate, et al, Smart Sensor System for Trace Organophosphorus and Organsulfur Vapor Detection Employing a Temperature-Controlled Array of Surface Acoustic Wave Sensors, Automated Sample Preconcentration, and Pattern.
Viscosity and Density Sensing with Ultrasonic Plate Waves, B.A. Martin, S.W. Wenzel, and R.M. White, Sensors and Actuators, A21-A23 (1990), 704-708.
"On-line Sensor for Density and Viscosity Measurement of a Liquid or Slurry for Process Control in the Food Industry" Margaret S. Greenwood, Ph.D. James R. Skorpik, Judith Ann Bamberger, P.E. Sixth Conference on Food Engineering, 1999 AiChE Annual Meeting, Dallas, Texas.
"Micromachined viscosity sensor for real-time polymerization monitoring", O.Brand, J.M. English, S.A. Bidstrup, M.G. Allen, Transducers'97, 121-124 (1997).
"Frequency repsonse of cantilever beams immersed in viscous fluids with applications to the atomic force microscope", J.E. Sader, J. Appl. Phys. 84, 64-76 (1998).
"Resonance response of scanning force microscopy cantilever", G.Y. Chen, R.J. Warmack, T.Thundat, and D.P. Allison, Rev. Sci. Instrum. 65, 2532-2537(1994).
"Lecture notes on shear and friction force detection with quartz tuning forks" Work presented at the "Ecole Thématique du CNRS" on near-field optics, Mar. 2000, La Londe les Maures, France by Khaled Karrai, Center for.
J. Sorab, G.S. Saloka: "Engine Oil Viscosity Swnsors Using Disks of PZT Ceramic as Electromechanical Vibrators" Society of Automotive Engineers SAE, No. 971702, 1997.
E. Bohmer, "Elemente der angewandten Elektronik", Aug. 1978, with English translation.
Zhang et al.: "Determination of Liquid density with a low frequency mechanical sensor based on quartz tuning fork" Sensors and Actuators B. Elsevier Sequoia S.A. Lausanne, CH. vol. 84, No. 2-3, May 15, 2002, pp. 123-128.
Shih et al.: Simultaneous Liquid Viscosity and Density Determination with Piezoelectric Unimorph Cantilevers: Journal of Applied Physics, American Institute of Physics. New York, U.S., vol. 89, No. 2, Jan. 15, 2001, pp. 1497-1505.
Dring et al.: "Integrated on-line multisensing of fluid flow using a mechanical resonator" Sensors and Actuators A, Elsevier Sequoia S.A., Lausanne, CH, vol. 85, No. 1-3, Aug. 25, 2000, pp. 275-279.
International Search Report dated Mar. 22, 2004 (PCT/US03/32982) 1012.183WO.
International Search Report dated Dec. 12, 2003 (PCT/US03/12503) 1012.171WO.
Greenwood et al., "Measurement of Viscosity and Shear Wave Velocity of a Liquid or Slurry for On-line Process Control", Ultrasonics 39 (2002) pp. 623-630.
"Sensors", www.izm.fhg.de, accessed on Oct. 3, 2002.
"Sensors and Actuators, INTELLEK Oil Condition Sensor", DELPHI Energy and Chassis Systems.
Muramatsu et al., "Viscosity Monitoring with a Piezoelectric Quartz Crystal and Its Application to Determination of Endotoxin by Gelation of Limulus Amebocyte Lysate", Mar. 8, 1988.
Langdon, "Vibratory Process Control Tranducers", The Marconi Review, Third Quarter, 1980, pp. 156-175.
Invitiation to Pay Additional Fees, PCT/US03/32983, mailed Apr. 8, 2004. (1012.192WO).
U.S. Appl. No. 09/420,334 entitled "Graphic Design of Combinatorial Material Libraries" (Lacy, et al.) filed on Oct. 18, 1999.
U.S. Appl. No. 09/305,830 titled "Synthesizing Combinatorial Libraries of Materials" (Rust, et al.) filed on May 5, 1999.
U.S. Appl. No. 09/755,623 entitled "Laboratory Datbase System and Methods for Combinatorial Materials Research" (Dorsett, Jr., et al.) filed on Jan. 5, 2001.
The family of applications for U.S. Appl. No. 09/174,856 titled "Graphic Design of Combinatorial Material Libraries" (Lacy, et al.) filed Oct. 19, 1998.

U.S. Appl. No. 09/550,549 entitled "Automated Process Control And Data Management System And Methods" (Crevier, et al.) filed on Apr. 14, 2000.
U.S. Appl. No. 09/800,819 entitled "Method and Apparatus for Characterizing Materials by Using a Mechanical Resonator" filed on Mar. 7, 2001.
U.S. Appl. No. 09/580,024 entitled "Instrument for High Throughput Measurement of Material Physical Properties and Method of Using the Same" filed on May 26, 2000.
U.S. Appl. No. 10/155,207 entitled "High Throughput Microbalance and Methods of Using Same" filed on May 24, 2002.
U.S. Appl. No. 09/285,963 entitled "Rapid Characterization of Polymers" (Safir et al.) filed on Apr. 2, 1999.
PCT International Search Report, dated Oct. 21, 2002, PCT/US02/17780 (1012-167WO).
Matsiev, "Application of Flexural Mechanical Resonators to Simultaneous Measurements of Liquid Density and Viscosity", 1999 IEEE UltraSonics Symposium, pp. 457-460.
Hammond et al., "Sensor", Department of Electrical and Computer Engineering, University of Maine, pp. 1342-.
Grate et al., "Smart Sensor System for Trace Organophosphorsu".
Karrai, "Lecture Notes on Shear and Friction Force Detection", Mar. 2000.
Nesbitt W. Hagood IV et al.., "Development of Micro-Hydraulic Transducer Technology", 10th International Conference on Adaptive Structures and Technologies, Oct. 11-13, 1999, Paris, France.
Pamphlet, "Hygroscopicity Measurement Apparatus," PUUMAN (no date).
Laine, E., and M. Aarnio, "Device for the Investigation of Humidy-related Behaviours of Materials," Department of Physics, University of Turku, no date.
Surface Acoustic Wave Hygrometer, http://technology.jpl.nasa.gov, accessed Mar. 16, 2002, 2 pages.
Hoenk, Michael, et al.., "Surface Acoustic Wave Hygrometer: Measuring Water Vapor in Earth's Atmosphere," http://mishkin.jpl.nasa.gov, accessed Mar. 16, 2002, 7 pages.
Trolier, Susan et al., "Preparation of Chemically Etched Piezoelectric Resonators for Density Meters and Viscometers", Mat. Res. Bull., vol. 22, pp. 1287-1274 (1987).
J.M. Hammond, R.M. Lee, D.G. Libby, XJ Zhang and L.A. Prager, "An Acoustic Automotive Engine Oil Quality Sensor", Transducers 97, S. 1343-1346.
H. Valimaki, J. Lekkala, H. Helle, "Evaluation of Equivalent Circuit Model for Thickness-Shear Mode Resonators in Liquids", Eurosensors X, Leuven, Belgium Nov. 9, 1996, S1377-1380.
H. Endo, K. Soda, I. Karube, H. Muramatsu, "Online Monitoring of the Viscosity in Dextran Fermentation Using Piezoelectric Quartz Crystal", Biotechnology and Bioengineering, vol. 36, S 636-641 (1990).
Mason W. P., Hill M., "Measurement of the Viscosity and Shear Elasticity of Liquids by Means of Torsionally a Vibrating Crystal", Transactions of A.S.M.E., 69 (1947) 359-370.
Barnes C., "An in vitro urea sensor using a torsion-wave crystal device", Sensors and Actuators B, 8 (1992) 143-149.
Schmitt N. et al., "A new method based on acoustic impedence measurments for quartz immunosensors", Sensors and Actuators B43 (1997) 217-233.
Senstronics "Storm 50 Joint Pressure and Temperature Specifications".
"Cantilever Sensor Research Tool for Science and Industry", diScentris, Veeco.
Benes et al., "Viscosity Sensor Based on a Symmetric Dual Quartz Thickness Shear Resonator", pp. 1-7. 2003.
NSF Award Abstract #0239151, Feb. 6, 2003, pp. 1-2.
Nussbaum, "An Accurate Non-Radioactive Fluid Density Sensor", presentation to the Society of Petroleum Engineers, Bergen, Norway, Apr. 1, 2003.
Fleming, The Vibrating Tuning Fork Fluid Density Tool, pp. H1-H15.
"The Lubri-Sensor Electronic Oil Quality Analyser", www.pmlubricants.com, accessed on Feb. 5, 2004.
"Sensor Technology Improves Jet Engine Reliability", www.afrlhorizons.com, accessed on Feb. 5, 2004.

"Oil Quality Sensor", www.sae.org, accessed on Feb. 5, 2004.

"Refrigerant Flow in Evaporators", www.heatcrafteom.com, accessed on Feb. 5, 2004.

"Theory of the Vibrating Tuning Fork Fluid Density Tool", www.lancs.ac.uk, p. 1, accessed on May 7, 2003.

"A Vibrating Tuning Fork Fluid Density Tool", www. smithinst.ac.uk, p. 1, accessed on Feb. 2, 2004.

"SINIMS Oil and Gas Workshop", Draft: Notes of presentations and discussions, ICMS, Edinburgh, Mar. 11, 2002.

"Field Trials of The Viscosity & Fluid Density Tools (VFD)", Nan Gall Technology, published Aug. 2002.

"ViscoMaster HFO Viscosity Transmitter for Marine and Power Applications", Solartron Mobrey.

"CJV-5000 Vibro Viscomteer Utilizing Tuning-Fork Technology", Yahoo Search accessed on Jun. 18, 2003.

"SOS-Smart Oil Sensor", Impact Technologies, LLC.

Pamplet by Kavlico-A Solectron Company, Capability Brochure Industrial Sensors and Tranducers.

A&D Weighing, SV Series Users' Handbook V1.04E, pp. 1-40.

"EPSON presents the MC-30A: Reliable 32.768kHz Dedicated to Automotive Applications", Aug. 25, 2003, www. epson.com, accessed on Feb. 11, 2004.

Lec et al., "A Remote Acoustic Engine Oil Quality Sensor", 1997 IEEE UltraSonics Symposium, pp. 419-422.

Zhang et al., "Contributions of Amplitude Measurement in QCM Sensors", IEEE Transactions on Ultrasonics, Ferroelectrics, and Frequency Control, vol. 43, No. 5, Sep. 1996, pp. 942-947.

Smith et al., Water Sorption Isotherms and Enthalpies of Water Sorption by Lysozyme Using the Quartz Crystal Microbalance/heat Conduction Calorimeter, BIOCHIMICA et Biophysica Acta, Oct. 4, 2001, pp. 150-159.

Ulbricht, Helmar, Crimpen-eine ausgereifte AnschluBtechnik.

International Search Report dated Aug. 4, 2004, PCT/US2004/008552.

Zeisel et al., A PRecise and Robust Quartz Sensor Based on Tuning Fork Technology for (SF6)- Gas Density Control, Elsevier Sciences, 2000.

* cited by examiner

ENVIRONMENTAL CONTROL SYSTEM FLUID SENSING SYSTEM AND METHOD

CLAIM OF BENEFIT OF FILING DATE

The present application claims the benefit of the filing date of U.S. Provisional Application Ser. No. 60/505,943 (filed Sep. 25, 2003) and International Application PCT/US03/32983 (filed Oct. 17, 2003), which are hereby incorporated by reference.

TECHNICAL FIELD

The present invention generally relates to the field of fluid sensors and more particularly to a fluid sensor incorporating a mechanical resonator adapted for and as used in an environmental control system, such as a refrigeration system or other temperature management system.

BACKGROUND OF THE INVENTION

The use of a quartz oscillator in a sensor has been described in U.S. Pat. No. 6,223,589. U.S. Pat. No. 5,741,961 also discloses a quartz resonator for use in an engine oil sensor. Yet another piezoelectric sensor for engine oil is disclosed in Hammond, et al., "An Acoustic Automotive Engine Oil Quality Sensor", Proceedings of the 1997 IEEE International Frequency Control Symposium, IEEE Catalog No. 97CH36016, pp. 72-80, May 28-30, 1997.

An improved system for measuring characteristics of fluids using mechanical resonators is disclosed in commonly-owned U.S. Pat. Nos. 6,401,519; 6,393,895; 6,336,353; and 6,182,499.

The use of acoustic sensors has been addressed in applications such as viscosity measurement in J. W. Grate, et al, Anal. Chem. 65, 940A-948A (1993)); "*Viscosity and Density Sensing with Ultrasonic Plate Waves*", B. A. Martin, S. W. Wenzel, and R. M. White, Sensors and Actuators, A21-A23 (1990), 704-708; "*Preparation of chemically etched piezoelectric resonators for density meters and viscometers*" S.Trolier, Q. C. Xu, R. E. Newnham, Mat.Res. Bull. 22, 1267-74 (1987); "*On-line Sensor for Density and Viscosity Measurement of a Liquid or Slurry for Process Control in the Food Industry*" Margaret S. Greenwood, Ph.D. James R. Skorpik, Judith Ann Bamberger, P. E. Sixth Conference on Food Engineering, 1999 AIChE Annual Meeting, Dallas, Tex.; U.S. Pat. Nos. 5,708,191; 5,886,250; 6,082,180; 6,082,181; and 6,311,549; and "*Micromachined viscosity sensor for real-time polymerization monitoring*", O.Brand, J. M. English, S. A. Bidstrup, M. G. Allen, Transducers '97, 121-124 (1997). See also, U.S. Pat. No. 5,586,445 ("*Low Refrigerant Charge Detection Using a Combined Pressure/Temperature Sensor*").

Notwithstanding the above, there remains a need in the art for alternative or improved sensors for analyzing fluids used in machines (such as those in residential, commercial, industrial, food service, and transportation vehicle environmental control systems), particularly for measuring changes in fluid amounts, changes in fluid quality or combinations thereof.

SUMMARY OF THE INVENTION

One embodiment of the present invention is a method for monitoring a thermal change fluid in an environmental control system. The method includes operating a mechanical resonator in an environmental control system selected from heating, ventilation, air conditioning and refrigeration systems. The environmental control system includes a passage for a thermal change fluid. The mechanical resonator is a flexural resonator, a torsional resonator or a combination thereof. At least a portion of the resonator is translated through the thermal change fluid. The thermal change fluid comprises R-134A refrigerant, a mineral oil, an ester lubricant or a mixture thereof. The response of the resonator to the thermal change fluid in the passage is monitored.

Another embodiment of a method of the present invention is for monitoring a superheat condition of a refrigerant in an environmental control system. The method includes superheating a refrigerant in an environmental control system. The superheated refrigerant is monitored with a mechanical resonator.

Still another embodiment of a method of the present invention is for monitoring a fluid in an environmental control system. The method includes pressurizing and heating a reduced pressure vapor in an environmental control system to form an elevated pressure, elevated temperature vapor. The elevated pressure, elevated temperature vapor is condensed to form an elevated pressure liquid. The elevated pressure liquid is expanded to form a reduced pressure liquid. The reduced pressure liquid is evaporated to form a reduced pressure vapor. A fluid selected from one or more of the elevated pressure, elevated temperature vapor, the elevated pressure liquid, the reduced pressure liquid, the reduced pressure vapor and combinations therof is monitored with a mechanical resonator.

One embodiment of an apparatus of the present invention is an environmental control system selected from heating, ventilation, air conditioning and refrigeration systems. The system has a passage containing a thermal change fluid. The thermal change fluid comprises R-134A refrigerant, a mineral oil, an ester lubricant or a mixture thereof. The system has at least one mechanical resonator for relative translation with the thermal change fluid. The mechanical resonator is a flexural resonator, a torsional resonator or a combination thereof. The system includes a circuit for monitoring a response of the resonator to the thermal change fluid.

Another embodiment of an apparatus of the present invention is a superheat monitoring system for use in an environmental control system comprising a refrigerant. The system has at least one mechanical resonator for contacting a superheated refrigerant in the environmental control system. The system has a circuit for monitoring a response of the resonator to the superheated refrigerant. The monitoring circuit includes a processing unit adapted to receive a signal from the resonator. The processing unit is programmed with an algorithm for monitoring the superheat condition of a fluid in the system.

Still another embodiment of the invention is an environmental control system. The system has a compressor for compressing a reduced pressure vapor to form an elevated pressure, elevated temperature vapor. The system has a condenser for removing heat from and condensing the elevated pressure, elevated temperature vapor to form an elevated pressure liquid. The system has an expansion device for reducing the pressure of the elevated pressure liquid to form a reduced pressure liquid. The system includes an evaporator for evaporating the reduced pressure liquid to form the reduced pressure vapor. The system has at least one passage for containing a refrigerant. The refrigerant comprises a fluid selected from one or more of the elevated pressure, elevated temperature vapor, the elevated pressure liquid, the reduced pressure liquid, the reduced pressure vapor, and combinations thereof. A mechanical resonator is positioned to contact the refrigerant in the passage. The system includes a circuit for monitoring the response of the resonator to the refrigerant in the passage.

Other objects and features will in part be apparent and in part pointed out hereinafter.

DETAILED DESCRIPTION

Figure 1:
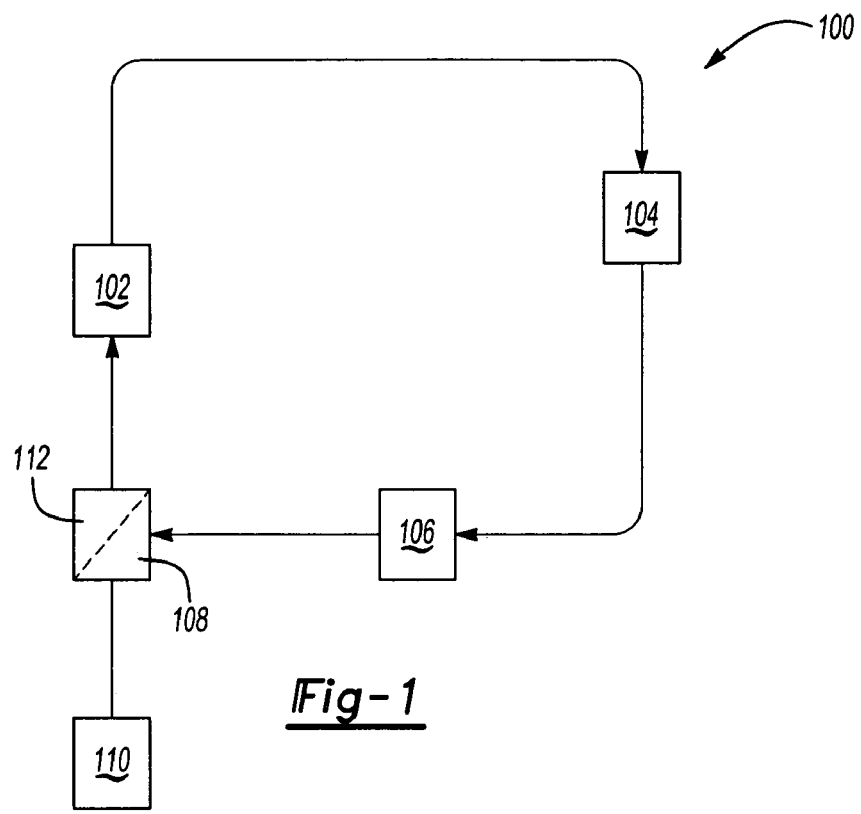
FIG. 1 shows a schematic view of one system of the present invention.

As will be appreciated from the description herein, the present invention is directed primarily for analyzing fluids that are contained (whether in a sealed system, an unsealed system or a combination thereof) in a cooling apparatus or other environmental control system. One specific use of the present invention is the analysis of fluids (and particularly the viscosity, density, viscosity/density product, conductivity or dielectric properties of fluids) that are used in an environmental control system adapted for residential building use, commercial building use, industrial use (e.g., as part of a power plant system), transportation vehicle use (e.g., as part of a passenger environmental control system, as part of an engine or other vehicle component environmental control system, combinations thereof or the like), such as fluids that are part of a sealed and/or self-contained operating system, and more specifically, fluids that are part of a circulating or reservoir fluid system.

As gleaned from the above, reference to an "environmental control system" in accordance with the present invention is not intended to limit the application of the present invention. Rather, "environmental control system" contemplates a system for application in heating, ventilation, air conditioning and refrigeration systems for residential use, commercial use, industrial use or two or more of the forenoted uses. "Environmental control system" may also contemplate a system for application in food processing, temperature management for food storage or material storage units (e.g., refrigerators, freezers, or the like). "Environmental control system" may further contemplate a passenger comfort system in transportation vehicles such as rail cars, ships, submarines, boats, aircraft, automotive vehicles, farming vehicles, earth-moving vehicles, heavy trucks, spacecraft, military vehicles, or the like. "Environmental control system" may also contemplate a system for controlling temperature in engines, other power plant devices, or other components (e.g., a radiator, an oil cooler, or both) for such transportation vehicles. "Environmental control system" may also contemplate another system, such as without limitation, chillers, nuclear, coal or gas fired power generation facility equipment environmental control system, incineration equipment environmental control system, industrial furnace environmental control system, reactors, baths, electronic component environmental control system, fluid dispensing system, ice rink system, materials processing heat treatment system, or otherwise. In short, the present invention contemplates application in any of a number of different types of environmental control systems, whether the systems are mobile, stationary or combinations thereof, or whether the environmental control system includes features such as humidity control, pressure control or otherwise.

To the extent that heat exchangers are contemplated as within environmental control systems, it will be appreciated that in many such systems, the heat exchanger system contains one or more fluids such as refrigerants or other heat transfer fluids, aqueous based coolants, refrigerant oils and lubricants (e.g., to lubricate internal moving parts for machines used to compress, regulate and move fluids), protective fluids for corrosion protection and leak detection or visualization fluids. Thus, it should be appreciated that the present invention also contemplates within its scope the employment of the present sensors to monitor not only fluids that are used for accomplishing heat exchange, but fluids that are used elsewhere in an environmental control system, such as in generators ("gensets") or motors used to drive compressors to move fluids for effecting temperature change.

Further in connection with the above, it should thus be appreciated that "thermal change fluid" refers not only to fluids that are regarded as refrigerants, but also to other heat exchange fluids, including but not limited to refrigerants, refrigerant lubricants, coolants (e.g., without limitation, a radiator fluid), combinations of two or more of such fluids. A fluid may be a liquid, a gas or a combination thereof. Examples include hydrocarbon refrigerants, chlorofluorocarbon refrigerants, hydrochlorofluorocarbon refrigerants, hydrofluorocarbon refrigerants, synthetic refrigerants, naturally occurring refrigerants, CFC-free refrigerants, combinations of two or more refrigerants, or the like. Even more specific examples include Freon®, ammonia, hydrogen, compressor oil, ethylene glycol, water, air, brine, tetrafluoroethane, R-134A, R-11, R-12, R-22, R-40, R-125, R-152A, R-170, R-290, R-406A, R-410A, R-404A, R-502, R-507, R-407C, R-290, R-600A, R-717, R-764, other National Refrigeration Safety Code Group I, II or III refrigerants, or the like. Thus, it should be appreciated that many such thermal change fluids are complex solutions or mixtures of components mentioned above, making it difficult to predict performance values over time. The ability of the present invention to reliably and reproducibly monitor performance of such fluids offers yet additional benefits.

Thus a thermal change fluid might be a fluid that changes state upon application or absorption of heat, and as a result, removes heat from a region to be cooled. It may also be a fluid that is initially cooled by an initial environmental control system, and then passed in the region to be cooled, and returned with accumulated heat to the initial environmental control system. One specific example of the latter type of fluid is substantially free of a lubricant.

The present invention is particularly attractive because of its ability to yield reproducible and reliable fluid analysis, particularly over a broad range of operation temperatures. It also affords a relatively low cost alternative to other existing sensors. In one particular embodiment, though not required in every embodiment, the sensors of the present invention can be operated with success at a relatively low frequency range. The present invention also affords the unique ability to operate in certain heretofore impractical applications where a reliable sensor would have been desirable, such as in the superheating of fluids.

The present invention is thus predicated upon the discovery of an improved method for analyzing a fluid contained within an environmental control system, comprising the steps of providing an environmental control system including a passage or reservoir for containing a fluid; placing a sensor including a mechanical resonator in the passage or reservoir; operating the resonator to have a portion thereof translate through the fluid; and monitoring the response of the resonator to the fluid in the passage or reservoir.

The present invention thus is directed in one particular aspect to a method for sensing a fluid in a circulating or reservoir thermal change fluid system, and includes the steps of providing a sealed circulating or reservoir fluid system; incorporating a mechanical resonator into the system, the mechanical resonator being in electrical communication with a source of an input signal; coupling the mechanical resonator with diagnostics hardware; exposing the fluid of the circulating or reservoir fluid system to the mechanical resonator; optionally applying an input signal; and monitoring a response of the mechanical resonator to the fluid with the diagnostics hardware.

When employed, the input signal for the sensors of the present invention may be any suitable signal. It may be generated from a direct current source or an alternating current source. It can be a constant frequency or a varying frequency. In one highly preferred embodiment, the signal is a varying frequency input signal. In another embodiment, the signal is a result of a voltage spike, sine wave burst, mechanical shock, pressure impulse, combinations thereof or the like.

The step of monitoring may be performed under any of a variety of different conditions. For example, in one embodiment, the monitoring step includes monitoring the change of frequency of the mechanical resonator while maintaining the input signal to the resonator as a constant. In another embodiment, the monitoring step includes monitoring the change in electrical feedback from the resonator while maintaining a constant frequency. In yet another instance, the monitoring can be in the substantial absence of a signal, where for example, the frequency change, the amplitude decay or both of a resonator is observed over a period of time after an input signal has been terminated.

The monitoring step will typically be guided by the nature of any input signal. In one embodiment, for example, the monitoring step includes varying the frequency of a variable frequency input signal over a predetermined frequency range to obtain a frequency-dependent resonator response of the mechanical resonator.

One or more frequency sweeps may be employed, with each respective sweep being the over the same range or a different range (e.g., smaller or larger than the previous range).

The sensor of the present invention preferably includes at least one mechanical resonator, still more particularly one that is capable of operating at a frequency range less than 1 MHz. For example, a highly specific resonator according to the present invention is operated at a frequency of less than 500 kHz, more specifically less than 100 kHz, and even still more specifically less than 75 kHz. A particularly specific operational range is from about 1 kHz to about 50 kHz and more specifically about 5 to about 40 kHz. One highly specific embodiment operates at about 20 to about 35 kHz.

Though other resonators are also possible, such as thickness shear mode resonators, surface acoustic wave resonators or the like, a specific exemplary resonator is selected from the group consisting of tuning forks (e.g., having two tines, or more tines such as a trident tuning fork), cantilevers, bimorphs, unimorphs, membrane resonators, disc benders, torsion resonators, or combinations thereof. A highly specific example of an attractive resonator is a tuning fork resonator, such as a two tine tuning fork or a trident tuning fork. For some applications, a tuning fork may be employed in which the geometry of the resonator is such that two tines each resonate in different planes relative to each other, such as perpendicular to each other.

The structure of the resonator may be any suitable structure taking into account the specific environment into which it is to be introduced. As indicated, a preferred resonator is a tuning fork, and thus will include a plurality of tines projecting from a common base wherein the tines and base may be arranged in a variety of configurations.

It will be also appreciated that the resonator of the present invention, though potentially free standing, will generally be carried by a suitable support medium, such as a connector device for connecting the resonator with a source of an input signal, a device for monitoring the response of the resonator to the signal, or both. The nature of the connector device may vary from application to application. In one embodiment, it is a molded plastic (e.g., polyamide or the like) device into which electrical wires can be inserted in electrical communication with an inserted resonator. The connector may itself be configured for providing a suitable attachment (e.g., using a quick-connect mechanism) to a surface of the machine into which it is introduced. Alternatively, the connector may be adapted for insertion into or otherwise may comprise an integrated portion of a receptacle within the machine. It is also contemplated that the connector device, the receptacle or both may include a chip (e.g., a computer chip) for assisting in the communication of date to other components described herein.

The present invention is not limited to the use of a single resonator, but rather a plurality of resonators may be used. There may be plural resonators that are operational over the same or a different range of frequencies. There may be a plurality of resonators each of a different material or having a different coating or surface treatment. Plural resonators may be carried by a common carrier, or by separate carriers. Further, the resonators may be placed in the same general or proximate region of the environmental control system or at remote locations relative to each other. An array of at least three resonators on a common carrier may also be employed.

As seen in FIG. 1, one embodiment involves the incorporation of a sensor according to the present invention into an environmental control system 100 that includes a compressor 102, a condenser 104 (e.g., a dual pass condenser) and an evaporator 106, through which a thermal change fluid is cycled via one or more passages, such as in a conduit. Other components may also be employed as desired, such as one or more suitable pumps, a filter, a dryer, a suitable flow cell, or a combination of two or more thereof. Likewise, any of the above components may be omitted from a system of the present invention. An expansion valve is typically employed. Other suitable valving may also be employed.

One or more of the sensors 108 according to the present invention is adapted for permanent or temporary placement within in one of the system components or between one of the system components. For example one or more sensors 108 may be situated between the compressor and the condenser, between the condenser and evaporator (as illustrated without limitation in FIG. 1), between the evaporator and the compressor, within one or more of the components (e.g., in the compressor oil sump), or combinations of two or more of such locations. Likewise, one or more sensors may additionally or alternatively be incorporated in another component, such as a conduit, coil, filter, nozzle, dryer, pump, valve or other component, or positioned upstream or downstream therefrom. The sensor may be located in the flow path of the thermal change fluid (e.g., in a conduit), a headspace or both. In a particular embodiment, the sensor is included along with (and optionally integrated therewith) a condition monitoring device such as a temperature measurement device, a pressure measurement device, a mass flow meter, or combinations of two or more of such devices. Without limitation, an example of a combined pressure and temperature sensor is discussed in U.S. Pat. No. 5,586,445 (incorporated by reference).

Accordingly, it will be appreciated that in one preferred embodiment, a system operates in which an elevated pressure, elevated temperature vapor is formed (e.g., in a compressor), heat is removed from the vapor to condense it to an elevated pressure liquid (e.g., in a condenser). The elevated pressure liquid is then reduced in pressure (e.g., in an expansion valve) and expanded to a lower pressure vapor (e.g., in an evaporator), and the system recycles. Optionally the liquid, vapor or both are filtered, dried or both. Sensing in accordance with a sensor of the present invention may be performed prior to or during formation of the elevated pressure, elevated temperature vapor, prior to or during formation of the elevated pressure, reduced temperature liquid, prior to or during expansion to the vapor, optionally during filtering, drying or both, or a combination of two or more such times.

Sensing in accordance with the present invention is particularly attractive for evaluating one or more of the level of a fluid (e.g., indicative of a system leak, a blockage in the system, or the like), the superheat condition of a fluid (e.g., the level of superheat), subcooling of a fluid, concentration of refrigerant in the fluid, concentration of anti-freezing component in the fluid, or the presence of contaminants in the fluid. In particular, the sensor is effectively employed to monitor (continuously or periodically) small changes in conditions of the fluid, such as viscosity, density, viscosity/density product, dielectric constant, conductivity or combinations of two or more thereof, which are indicative of a change of state of the fluid or the presence of contaminants, and to output the results thereof.

Optionally, the sensor, the condition monitoring device or both are in signaling communication with a processing unit 110 (which may include a user interface) for controlling operation of the environmental control system. The processing unit optionally is also in signaling communication with a condition monitoring device 112 (shown as part of an integrated assembly (e.g., a common fixture such as a manifold), but which can be split into one or more separate devices, which may be located at the same site as, upstream, downstream, or combinations thereof, as the sensor 108). Thus, data obtained from the sensor may be processed along with other data to assist in monitoring and establishing operating conditions of the environmental control device. Of course, other environmental control systems are also possible and the above illustration is not intended as limiting.

Thus, for example, in one aspect of the present embodiment, a sensor according to the present invention is employed to monitor at least one property of the thermal change fluid (e.g., the simultaneous monitoring of viscosity and density). Data obtained from the condition monitoring device (e.g., temperature, pressure, flow rate, or combinations) is communicated to the processing unit 110 along with the signal response from operation of the sensor. From the data provided, the processing unit, which typically will be programmed with a suitable algorithm, will process the data, and perform at least one operation of the environmental control system selected from switching the environmental control system or one or more components therein to an on or off state, closing or opening a valve in the environmental control system, changing a flow rate of the refrigerant, changing a pressure of the refrigerant, changing the operating speed or condition of one or more components of the environmental control system, otherwise controlling operation of the environmental control system or a component thereof, providing a visual output signal, providing an audible output signal, or a combination thereof. For example, in connection with operating a system employing a superheated refrigerant, it is contemplated that data obtained from the mechanical resonator is used to perform an operation selected from switching on a compressor, switching off a compressor, operating an expansion valve, selecting the appropriate number of operating compressor cylinders, or a combination thereof.

In this manner, it will be seen that many advantageous operations are possible by use of the present invention, including but not limited to the use of a sensor of the present invention to monitor the superheat condition of a thermal change fluid by correlating viscosity and density measurements observed with observed measurements for temperature, pressure or both. The nature of the sensing that is performed by the sensor can be varied depending upon the parameter or condition that is desired to be monitored. Among the various other applications are the use of the sensors herein for detecting the presence or absence of a fluid, the level of a fluid, the physical properties of a fluid, the presence of a contaminant in the fluid, the fluid pressure, the fluid flow rate, the fluid temperature, physical property, a change in physical property, condition or parameter of a fluid or a combination thereof.

Of course, basic conditions of the fluid such as viscosity, density, viscosity/density product, dielectric constant, conductivity or a combination thereof may also be monitored and reported, and in a highly specific embodiment, these are the properties that are analyzed.

It will be appreciated that the above configuration of FIG. 1 permits the use of one or more measurement modes (which can be measured using electrical techniques, optical techniques or a combination thereof) such as excitation at one or more frequencies around resonance, passive oscillations due to ambient noise, vibrations, EMI or the time decay of oscillation after an electrical or mechanical impulse (e.g., a voltage spike).

The sensors of the present invention may be used continuously. Alternatively, they can be disposable, so that at predetermined intervals it is removed and replaced with a different sensor.

The step of monitoring may be performed under normal operating conditions of the machine into which the present sensor is placed. The present invention is particularly advantageous in that it operable over a broad range of temperatures. Thus, in one specific aspect, it is contemplated that the monitoring step occurs at a temperature below −40° C. or possibly the monitoring step occurs at a temperature above 400° C. Generally the monitoring will occur between these extremes.

It is also possible that during or following a monitoring step the response of the sensor is compared against another value, such as a prior response of the resonator, a response of another resonator located elsewhere in the system, a known reference value for the fluid, or a combination of two or more such comparisons. For example, in the context of thermal change fluid, fresh fluid can be analyzed upon its introduction into an environmental control system. The observed response may then be stored in memory or otherwise recorded. It may also be possible to have data about a particular fluid stored in memory of a suitable processor, which can be retrieved in response to a triggering event, such as inputting by a technician or reading of a fluid type by an optical detector, such as a bar code scanner.

As the fluid is used, further analysis can be made and the response compared with those of the fresh fluid. The identification of a difference between responses could then be used as a trigger or other output signal for communicating with diagnostics hardware, which would provide an audible or visual signal to the operator. It is also possible that a signal is outputted to a remote telemetry device, such as one located external of the system. Thus, as with any of the embodiments herein a "wireless" communications system might be employed, pursuant to which a signal that is outputted may be a radiofrequency signal or another electromagnetic signal.

Comparison against reference values from the original fluid is not the only approach for generating a communication to a user about the fluid condition. It may be possible to pre-program certain expected values into a device, which then compares the real-time values obtained. Moreover, it is possible that no comparisons are made, but rather upon obtaining a certain threshold response, an output signal is generated for triggering a user notification, for triggering a system control unit to alter one or more functions of the system or a combination thereof. It is also contemplated that a sensor in a controlled fluid sample may be employed as an internal reference.

It is also possible that the response obtained from the monitoring is stored in a memory, with or without communicating the response to the user. In this manner, a service technician can later retrieve the data for analysis.

It should be appreciated that, by use of the term "passage" herein, it is not intended to limit to structures that would be defined by walls of a conduit. Passage may include a reservoir, a well, an open-channel, a closed-channel, a container, or the like. Thus, generally the term "passage" herein contemplates any structure into which a fluid may be introduced, contained temporarily, contained permanently, passed through, removed from or otherwise.

Incorporation into an automotive vehicle is in accordance with the inventive principles herein, therefore, it will be appreciated that the location of the resonator or plurality of resonators may be any suitable location for the intended measurement. Locating a resonator within a passage thus encompasses (among others) the location of a resonator in a conduit, a manifold, a sump, a filter device, or any other suitable location. Preferably the resonator is surface mounted, suspended or both, and positioned so that is analytical capability is not substantially compromised by fluid velocity, turbulence, mechanical oscillations, harmonics, vibrations or other extreme operating condition. If necessary to be subjected to an extreme operating condition, then preferably the resonator will be suitably housed (e.g., in an enclosed chamber) or otherwise shielded as described herein.

Diagnostics hardware for use in monitoring the response of a resonator according to the present invention may comprise any suitable art-disclosed hardware, and the discussion herein is not intended as limiting. Without limitation, it is possible to employ hardware such as disclosed in commonly owned U.S. Pat. Nos. 6,401,519; 6,393,895; 6,336,353; and 6,182,499, hereby incorporated by reference. Another approach herein for measurement hardware is to employ an electrical readout system in communication with a computer and any resonators. For example, one or more hard-wired circuits may be employed, or more preferably, one or a plurality of printed circuit boards is employed to comprise the readout board, thereby affording a compact and reliable structure. An application specific integrated circuit might also be employed in the present invention for signal generation, data acquisition or both. An example of one such device is illustrated in commonly owned U.S. application Ser. No. 10/394,543 (filed Mar. 21, 2003) (incorporated by reference). In addition, the hardware might also be part of or include a field programmable gate array (FPGA).

It should be appreciated that to the extent that the discussion herein, in conformance with the drawings, is specifically addressed to a system including one sensor adapted for analysis of a single fluid, the invention is not intended to be limited thereby. It will be appreciated that the present invention also covers the use of a plurality of different sensors for measuring one fluid or a plurality of different fluids.

Figure 2:
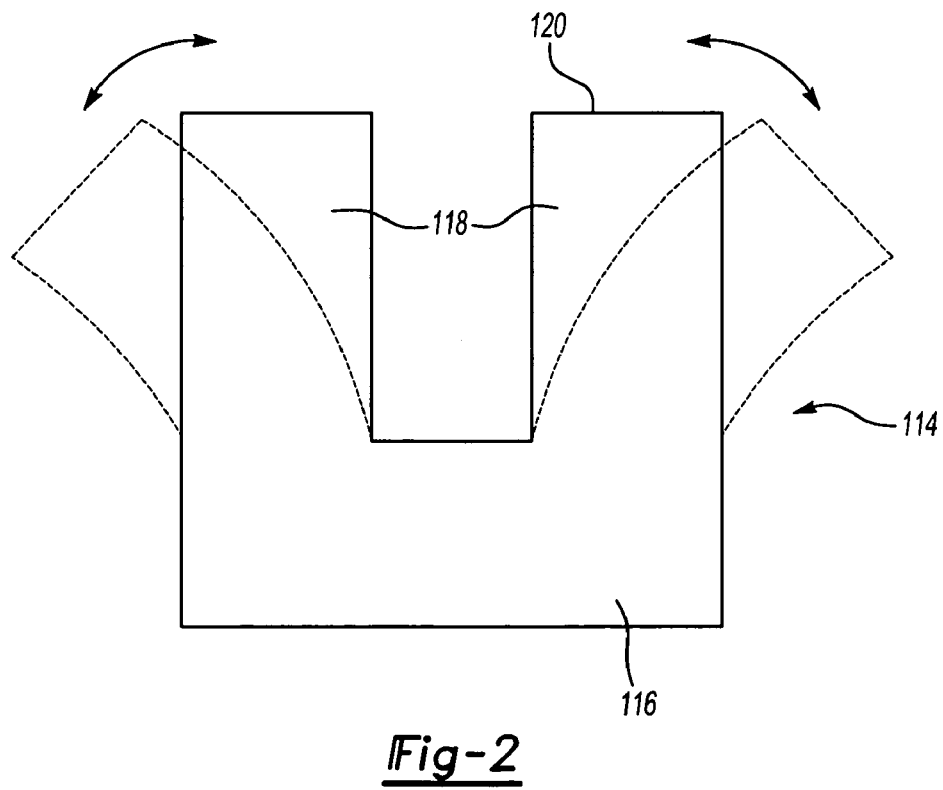
FIG. 2 shows a view of an illustrative resonator element of the present invention.

Turning now to FIG. 2, there is shown an illustration of one preferred resonator element 114 in accordance with the present invention. The resonator element 114 preferably includes a base 116 that has at least two tines 118 having tips 120 that project from the base. The shape of the tines and their orientation relative to each other on the base may vary depending upon the particular needs of an application. For example, in one embodiment, the tines 118 are generally parallel to each other. In another embodiment the tines diverge away from each other as the tips are approached. In yet another embodiment, the tines converge toward each other. The tines may be generally straight, curved, or a combination thereof. They may be of constant cross sectional thickness, of varying thickness progressing along the length of the tine, or a combination thereof.

Resonator elements are suitably positioned in an element holder. Alternatively, the elements (with or without a holder) may be securably attached to a wall or other surface defining one of the passages into which it is placed. In yet another embodiment, the element is suitably suspended within a passage 104, such as by a wire, screen, or other suitable structure.

Element holders may partially or fully surround the elements as desired. Suitable protective shields, baffles, sheath or the like may also be employed, as desired, for protection of the elements from sudden changes in fluid flow rate, pressure or velocity, electrical or mechanical bombardment or the like to help locate an element relative to a fluid or combinations thereof. It should be appreciated that resonator elements may be fabricated from suitable materials or in a suitable manner such that may be employed to be re-useable or disposable.

Examples of approaches to materials combinations, or the packaging of sensors that may be employed in accordance with the present invention are disclosed, without limitation in commonly-owned U.S. Provisional Application Ser. Nos. 60/456,767 and 60/456,517 (both filed Mar. 21, 2003) (and incorporated by reference). Thus, one particular approach contemplates affixing a sensor having a exposed sensing surface to a platform, wherein a spaced relationship is created between the exposed sensing surface and the platform. A suitable protective layer may be applied to cover the platform and/or the sensor while maintaining an exposed sensing surface. The latter exposed sensing surface may be prepared by the use of a consumable protective layer (e.g., a polymer, starch, wax, salt or other dissolvable crystal, low melting point metal, a photoresist, or another sacrificial material) that is used to block the exposed sensing surface prior to applying the protective layer.

One or both of the resonator element holders preferably is configured with suitable hardware so that the resonator can be connected in signaling communication with an input signal source, an output analyzer or a combination thereof. One preferred construction thus contemplates a device in which an exposed resonator is formed integrally with or attached to a chip or like surface mountable substrate that optionally has suitable circuitry built thereon. The chip, in turn, may also include other sensing elements, or may be attached in signaling communication with another substrate having sensing elements associated with it.

The resonators holders may be configured for temporary placement into a passage, such as by use of potted connector incorporating two or more wires.

A highly preferred embodiment of the present invention contemplates employing a tuning fork as a resonator for the resonator elements. Preferably a two tine tuning fork is employed as the resonator. However, the method and system of the present invention can use any type of tuning fork resonator, such as a trident (three-prong) tuning fork or tuning forks of different sizes, without departing from the spirit and scope of the invention.

As indicated, the present invention is not intended to be limited to tuning fork resonators. Other types of resonators can be used, such as tridents, cantilevers, torsion bars, bimorphs, membrane resonators, torsion resonators, unimorphs or combinations thereof. Still other types of resonators can be used if modified from their conventional art disclosed forms or if they are used in combination with a preferred resonator. Examples of such resonators include thickness shear mode resonators, length extension resonators, various surface acoustic wave devices or combinations thereof. A plurality of the same type or different types of resonators of resonators can be used in combination. For example, a low frequency resonator may be employed with a high frequency resonator. In this manner, it may be possible to obtain a wider range of responses for a given sample.

Specifically it is preferred that the resonator of the sensors of the present invention are mechanical resonators, and more preferably flexural resonators, torsional resonators or a combinaton thereof. In one embodiment, preferred resonators may be selected from the group consisting of tuning forks, cantilevers, unimorphs, bimorphs, disc benders, and combinations thereof.

The size of the resonators can be varied. However, it should be appreciated that one advantage of the present invention is the ability to fabricate a very small sensor using the present resonators. For example, one preferred resonator has its largest dimension smaller than about 2 cm, and more preferably smaller than about 1 cm. One resonator has length and width dimensions of about 3 mm by 8 mm, and possibly as small as about 1 mm by 2.5 mm. Geometry of the resonator may be varied as desired also. For example, the aspect ratio of tines of the tuning forks, or geometrical factors of other resonators can be optimized in order to achieve better sensitivity to the properties of the gas phase, liquid phase or its particular components (e.g., a lubricant).

For example, the aspect ratio of a tuning fork tine may range from about 30:1 to about 1:1. More specifically, it may range from about 15:1 to about 2:1.

Figure 3A:
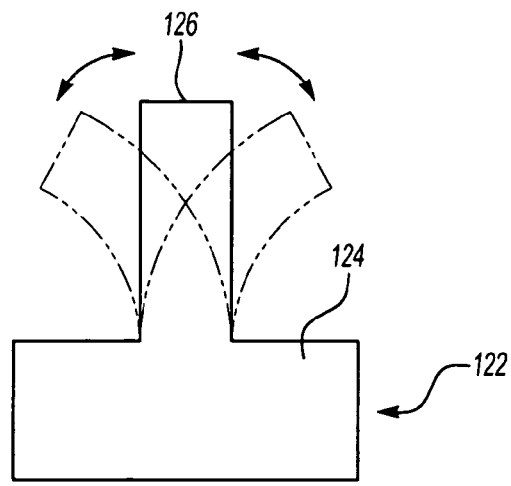
FIGS. 3A-3G illustrate alternative structures for a resonator according to the present invention.

It is thus seen that a preferred resonator is configured for movement of a body through a fluid. Thus, for example, as seen in FIG. 2, the resonator may have a base and one or a plurality of tines projecting from the base. It is preferred in one aspect that any tine has at least one free tip that is capable of displacement in a fluid relative to the base. FIG. 3A illustrates a cantilever 122 having a base 124 and a free tip 126. Other possible structures, seen in FIGS. 3B and 3C contemplate having a disk 128, a plate 130 or the like that is adapted so that one portion of it is displaceable relative to one or more variable or fixed locations 132 (132'). As seen in FIG. 3D, in yet another embodiment a resonator 134 is contemplated in which a shear surface 136 of the resonator has one or more projections 138 of a suitable configuration, in order that the resonator may be operated in shear while still functioning consistent with the flexural or torsional resonators of the present invention, by passing the projections through a fluid.

Figure 3B:
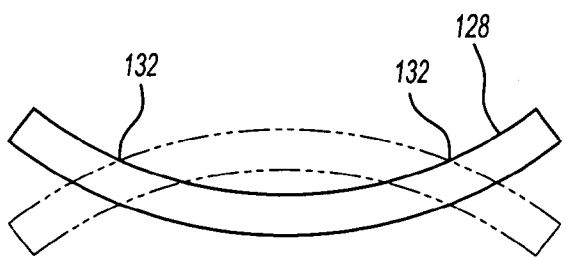
Figure 3C:
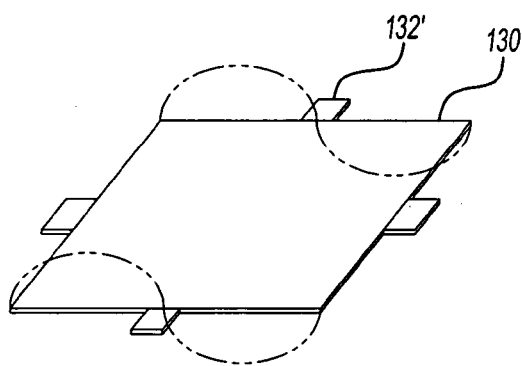
Figure 3D:
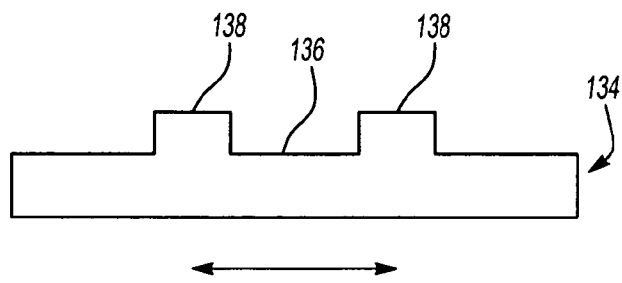
Figure 3E:
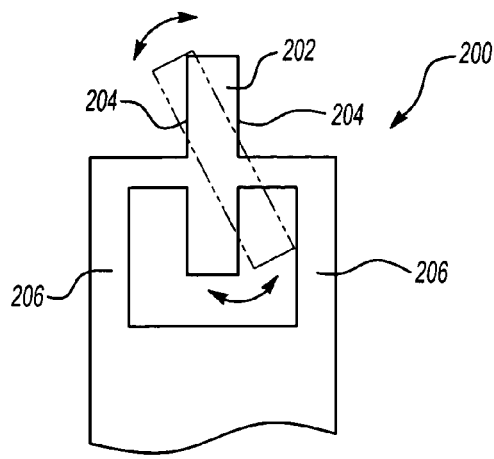
Figure 3F:
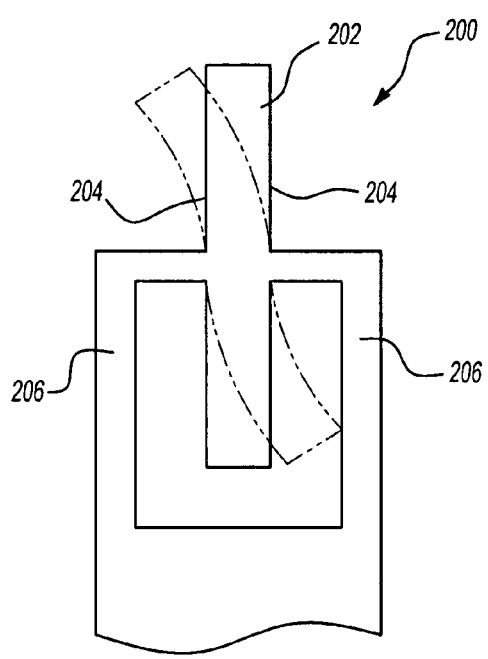
Figure 3G:
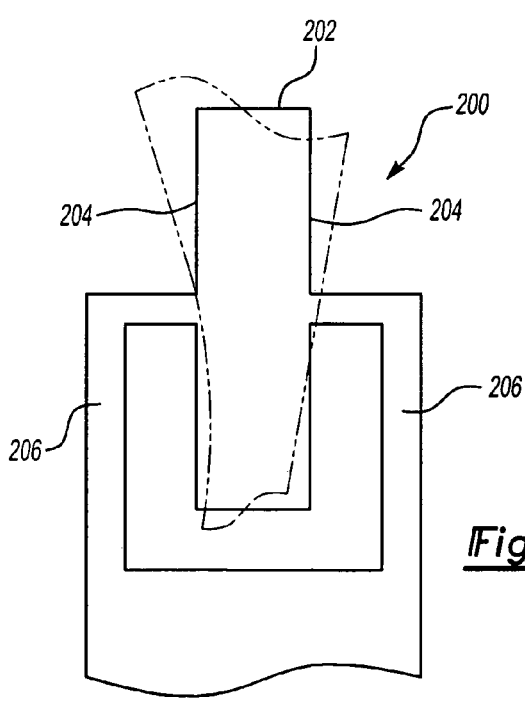

In still other embodiments, and referring to FIG. 3E-3G, it is contemplated that a resonator 200 may include an elongated member 202 supported on its sides 204 by a pair of arms 206. As shown respectively in FIGS. 3E-3G, the elongated member may be configured to oscillate side-to-side, back and forth, in twisting motions or combinations thereof.

The embodiment of FIG. 3B may be constructed as a monolithic device. Yet another structure of the present invention contemplates the employment of a laminate or other multi-layer body that employs dissimilar materials in each of at least a first layer and a second layer, or a laminate comprised of layers of piezoelectric material of different orientations or configurations. According to this approach, upon subjecting one or more of the layers to a stimulus such as temperature change, an electrical signal or other stimulus, one of the materials will respond different than the other and the differences in responses will, in turn, result in the flexure of the resonator. In yet another embodiment, it is contemplated that plural resonators can be assembled together with an electrode at least partially sandwiched therebetween. In this manner, it may be possible to further protect electrodes from harsh conditions, while still achieving the desired flexure. One specific example might include a two or more lithium niobate or quartz tuning forks joined together with a gold electrode therebetween. Other configurations (e.g., an H-shaped resonator) and material combinations may be employed as well, as disclosed in U.S. Provisional Application Ser. Nos. 60/456,767 and 60/456,517 (both filed Mar. 21, 2003), incorporated by reference.

As can be seen, the selection of the specific resonator material, structure, or other characteristic will likely vary depending upon the specific intended application. Nonetheless, it is preferred that for each application, the resonator is such that one or a combination of the following features (and in one highly preferred embodiment, a combination of all features) is present:

1) a coating, if placed upon the resonator in a thickness greater than about 0.1 micron, will not substantially detract from resonance performance;
2) the resonator is operable and is operated at a frequency of less than about 1 MHz, and more preferably less than about 100 $kH_z$;
3) the resonator is substantially resistant to contaminants proximate to the sensor surface;

4) the resonator operates to displace at least a portion of its body through a fluid; or 5) the resonator responses are capable of de-convolution for measuring one or more individual properties of density, viscosity, viscosity/density product, conductivity or dielectric constant.

The resonator may be uncoated or coated or otherwise surface treated over some or all of its exterior surface. A preferred coating is a metal (e.g., a conductive metal similar to what may be employed for electrodes for the sensor, such as silver, gold, copper, aluminum or the like), plastic, ceramic or composite thereof, in which the coating material is substantially resistant to degradation from the fluid to which it is to be exposed or to surface build-up, over a broad temperature range.

For example, one preferred embodiment, contemplates the employment of a base resonator material and a performance-tuning material. Among the preferred characteristics of the resonators of the present invention is the base material is generally thermally stable. For example, in one preferred embodiment, the material exhibits a dielectric constant that is substantially constant over a temperature range of about 0° C. to about 100° C., more preferably about −20° C. to about 150° C., and still more preferably about −40° C. to about 200° C. For example, it is contemplated that a preferred material exhibits stability to a temperature of at least about 300° C., and more preferably at least about 450° C. In another aspect, the dielectric constant of the performance-tuning material preferably is greater than that of quartz alone, such as by a factor of 5 or more, more preferably by a factor of 10 or more and still more preferably by a factor of 20 or more.

A highly preferred base material will not undergo a phase transformation up to a temperature of at least 500° C., and more preferably at least 1000° C. The base material may include a piezoelectric material, an electrostrictive material, a magnetostrictive material, a piezoresistive material, an elasto-optic material, an anisotropic material, or combinations thereof. By way of example, the particular material may be a metallic material, a crystalline material, a ceramic material or a combination thereof. Particular examples of base materials include, without limitation, quartz, lithium niobate, zinc oxide, lead zirconate titanate (PZT), gallogermanates (e.g., Langasite ($La_3Ga_5SiO_{14}$), Langanite, or Langatate), diomignite (lithium tetraborate), bismuth germanium oxide gallium phosphate, gallium nitride, aluminum nitride or combinations thereof.

A preferred characteristic of the performance tuning material is that it is relatively hydrophobic and exhibits a relatively low porosity, e.g., less than about 5% of its volume, more preferably less than about 3% and still more preferably less than about 1% and even still more preferably less than about 0.1%. A preferred performance tuning material will be stable at about 150° C. Preferably it will be resistant to absorption of oils.

Examples of particularly preferred performance-tuning materials include one or a combination of two or more materials selected from the group consisting of polymers, ceramics, diamond, diamond-like carbon (e.g., Diamonex® DLC or another amorphous carbon, such as hydrogenated amorphous silicon), and combinations thereof. For example, preferred performance-tuning materials might include one or a combination of two or more materials (e.g., specifically for exhibiting high hydrophobicity, a low coefficient of friction, or a combination thereof), selected from the group consisting of fluoropolymers (e.g., PTFE, a fluorinated carbon, a fluorosilicone, a fluoroether (one example being NOVEC™ from 3M), or the like), silicones, silanes (e.g., trimethyl silane or the like), siloxanes, polyolefins parylene, carbides (e.g., metal carbides), nitrides, oxides, diamond, diamond-like carbon, and combinations thereof; and more particularly might include one or a combination of two or more materials selected from the group consisting of polytetrafluoroethylene, fluorosilicone, polyethylene (e.g., high density polyethylene), polypropylene (e.g., high density polypropylene), silicon carbide, silicon nitride, diamond, diamond-like carbon, and combinations thereof. It is also possible that a material selected from the above identified examples of base materials may be employed as a performance tuning material.

It can thus be seen that the morphology of the resonators and any performance tuning material may vary. Amorphous materials might be employed in one or both devices, as may be polycrystalline materials, monocrystalline materials or a combination thereof.

The performance tuning materials of the present invention can be incorporated into a resonator in any of a number of different forms. By way of example, the performance tuning materials might be applied as one or a plurality of layers partially overlying a base resonator material; as one or a plurality of layers entirely overlying a base resonator material; as the entirety of the resonator material; as an intermediate layer in the resonator; as a matrix material having a different material dispersed therein; as a material dispersed within a different matrix material; or combinations thereof. When employed as a layer, the performance tuning material may be employed continuously or intermittently, along edges of the resonator base material, within the interior of the resonator base material, or a combination thereof. One or more of the performance tuning materials may also be employed to coat electrodes of sensors (which are typically going to be a precious metal, such as gold or silver, or another conductor) in accordance with the present invention.

One or a plurality of layers of the performance tuning materials therefore may be fabricated into a resonator using any of a number of different art-disclosed techniques, such as one or a combination of solvent coating, laser ablation, plasma deposition, physical vapor deposition, chemical vapor deposition, in situ polymerization, dipping, adhesive bonding, sintering, plating, fastening, chemical bonding or a combination thereof. By way of example, in one embodiment, a surface coating is applied to a resonator by masking the resonator and depositing performance-tuning material over the unmasked region. A step of photolithography may also be employed using suitable photoresist in order to achieve even more precise control over the size and shape of the coating. Preferably the deposition processing temperature is maintained below about 500° C., and more preferably below about 250° C.

Any coating process may also be accompanied with a suitable cleaning step, such as a rinse or wipe with a suitable solvent, such as water, alcohol or the like, and optional ultrasonic cleaning. A polishing step might also be employed.

In one embodiment a plurality of resonators are fabricated upon a common substrate and the resonators are separated from each other after fabrication by suitable separation techniques, such as cutting or the like. For example, in one aspect, the resonators are prepared by art-disclosed processing techniques, such as are practiced in the semiconductor device fabrication industry. Thus, a wafer may be provided, one or more layers deposited thereon (e.g., by vapor deposition, sputtering, spin coating, curtain coating, laminating wafer bonding, or the like). Steps may be performed for shaping the resonator, such as photolithography, laser cutting, etching, dicing or the like. Other fabrication techniques, such as casting, molding, or the like may also be used.

In a highly preferred embodiment in which the performance tuning material or other coating is deposited as a layer onto a surface of another material, the layer thickness preferably ranges up to about 10 μ, and more preferably is about 0.005 μ to about 5 μ, and more preferably is about 0.1 μ to about 1 μ.

Also as discussed, in certain instances it is preferable for the resonator to be optionally coated with a material to change the performance characteristics of the resonator. For example, the material can be a coating, such as to protect the resonator from corrosion, degradation or other factors potentially affecting resonator performance. Alternatively, it may be a specialized "functionalization" coating that changes the resonator's response if a selected substance is present in the composition being tested by the resonator. For example, adding a hydrophobic or hydrophilic functionality to a resonator tine allows the tine to attract or repel selected substances in the fluid being analyzed, changing the mass, effective mass, geometry or a combination thereof of the tuning fork and thereby changing its resonance frequency.

Thus, in one particularly preferred embodiment the resonators used in the present invention include a surface that is substantially resistant to contaminant build-up (e.g., impurities, soot, varnish, sludge, or the like) over all or a portion thereof. Accordingly, it is preferred that at least or portion of the resonator surface includes a material or texture that exhibits a relatively low affinity to contaminant, relatively high affinity to the fluid under test, a relatively high degree of hydrophobicity, or a combination thereof. Under separate circumstances, however, it may be desirable that the resonator surface include a material or texture that exhibits a relatively high affinity to contaminant, and a relatively high degree of hydrophilicity.

The resonators can also be functionalized with a polymer layer or other selective absorbing layer to detect the presence of specific molecules. The coating or functionality can be applied onto the resonator using any known method, such as physical vapor deposition (PVD), chemical vapor deposition (CVD), plasma enhanced chemical vapor deposition (PECVD), pulsed laser deposition (PLD), spraying or dipping. Further, the specific material selected for the coating or functionality will depend on the specific application in which the resonator is to be used.

A single resonator may be coated or functionalized. Alternatively, multiple resonators having the same or a different structure but different performance tuning materials, other coatings, functionalities or combinations thereof can be incorporated into one sensor. For example, a plurality of resonators may have the same structure but have different functionalities, each functionality designed to, for example, bond with a different target molecule. When the sensor is used in such an application, one resonator can, for example, be functionalized with a material designed to bond with a first substance while another resonator can be functionalized with a material designed to bond with a second substance. The presence of either one of these substances in the sample composition being tested will cause the corresponding resonator to change its resonance frequency. It is also possible to employ one or more sensors in which one resonator is coated, and another is not coated.

As discussed elsewhere, the manner of operating the sensors of the present invention may vary. In one embodiment, the sensor is operated continuously. In another, it may be intermittently operated. It is possible that the sensor may be operated only in preselected conditions, such as prior to starting system operation, upon starting system operation, during system operation, upon concluding system operation, or otherwise.

Under any or all of the above conditions, it will be recognized that the integrity of the measurement may be impaired as a result of some environmental condition, such as temperature. The present invention thus also contemplates as one of its embodiments, the employment of an environment conditioner, pursuant to which at least the environment proximate the location of the sensor is monitored or controlled to a predetermined condition. For example, it may be preferred with certain sensors to maintain the optimal sensing capability to be within a certain range of temperatures. A fluid that is outside of that range preferably will be detected and a temperature regulating device will heat or cool the fluid appropriately so that it can be efficiently sensed by the resonators of the present invention.

It is also possible that the environmental conditioner is operated to maintain the environment in a constant condition. In this manner, it can be seen, for example, that it is possible to employ a sensor of the present invention with a suitable heater for heating a frigid fluid to a certain temperature and preferably maintaining the fluid at that temperature for the duration of a measurement.

The employment of an environmental conditioner also offers the advantage that certain environmental condition—sensitive properties of the sensed fluid (e.g., the temperature dependency of viscosity) will be relatively unaffected during measurements, and provide a more reproducible and reliable data.

In certain instances, it is contemplated that data obtaining from the sensors may be graphically displayed, such as on a video display screen (e.g., a desk-top screen, a hand-held screen, or both). It may also be outputted in printed format, as will be seen with reference to the Examples.

Figure 5:
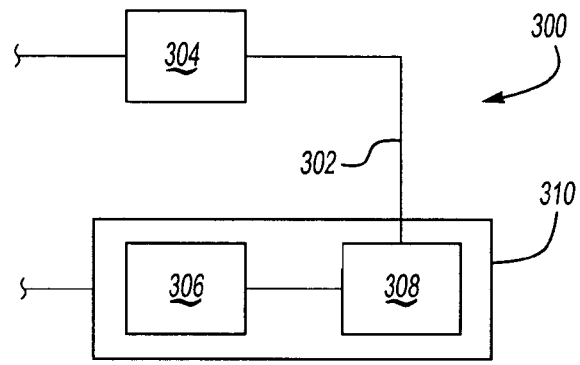
FIG. 5 illustrates an example of a sensing system in accordance with the present invention.
Figure 6:
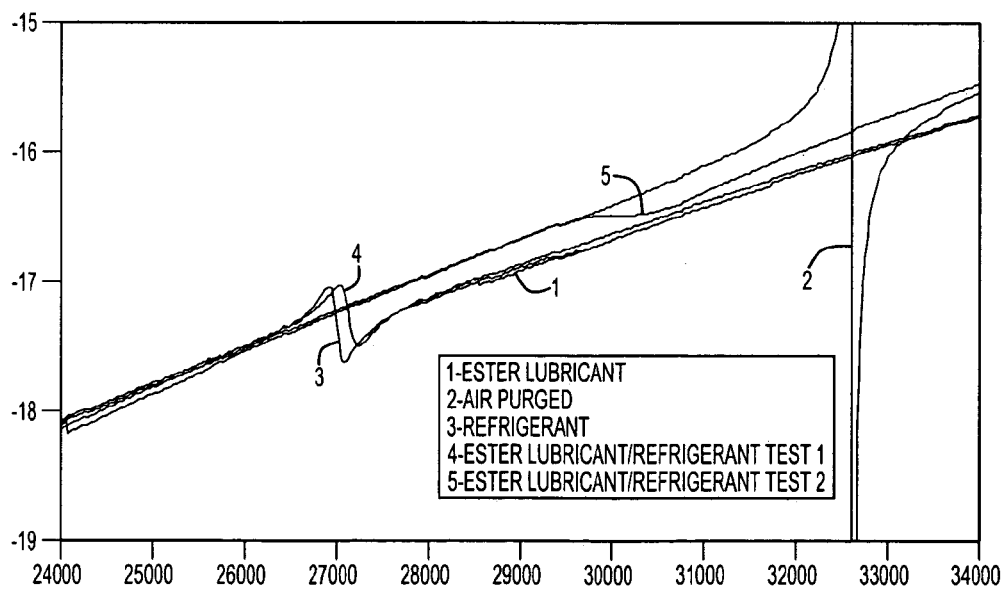
FIGS. 6 and 7 illustrate examples of data obtainable using the present invention.

Examples of suitable systems that may be employed herein include the systems illustrated in FIGS. 5 and 6 of 60/419,404 (filed Oct. 18, 2002 (incorporated by reference), as well as the systems described in U.S. application Ser. No.10/394,543 (filed Mar. 21, 2003) (incorporated by reference).

For example, one system employs a signal generator such as a sweep oscillator in signaling communication with a resonator. The signal generated from the resonator might be transmitted to an analog-to-digital converter. Data from another sensor may also be sent to the converter. The converter (if used), the sweep oscillator or both communicate with a suitable processor (e.g., an embedded microcontroller), which may in turn is in signaling communication with one or both of an internal bus or external bus, via for example a suitable interface (e.g., a CAN interface). Another possible system further includes a suitable environmental conditioner driven by a suitable driver in communication with the processor.

It will be appreciated from the foregoing that, in one preferred embodiment, the present invention is employed for sensing the condition of a thermal change fluid, and is founded upon analysis of changes in resonance characteristics that occur when the resonator is in contact with a thermal change fluid. The response is thus correlated with one or more fluid properties. Without intending to be bound by theory, to help with such a correlation, in a highly preferred embodiment, applicable for highly preferred resonators in accordance herewith, a mathematical or equivalent electrical circuit model can be constructed that includes the mechanical and electrical characteristics of the resonator, the properties of the surrounding fluid, and the coupling between resonator and fluid. Comparison of the model to measured data can help to yield the properties of interest. The parameters of the model can be found by fitting to the measured response using standard data fitting methods, such as (without limitation) least squares minimization. In one procedure, the parameters corresponding to the resonator alone are first determined by calibration in air or vacuum. A second calibration in a liquid of known properties such as viscosity, density, viscosity/density product, dielectric constant, conductivity or a combination thereof, gives parameters for mechanical and electrical coupling between resonator and liquid. With the model parameters then established, the properties of other liquids can be determined. Data acquisition and analysis can be simplified for incorporation in a fluid monitoring system.

Figure 4:
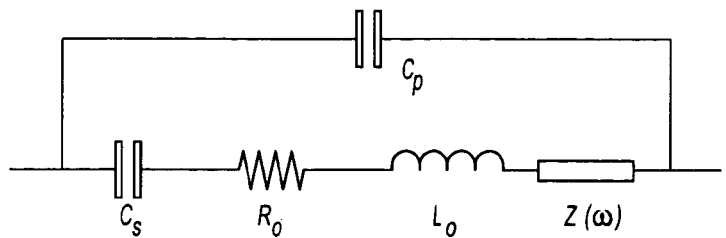
FIG. 4 illustrates an example of an equivalent circuit in accordance with the present invention.

An example of one such analysis is set forth in L. F. Matsiev, "*Application of Flexural Mechanical Resonators to Simultaneous Measurements of Liquid Density and Viscosity*", IEEE Ultrasonics Symposium Proceedings, pp. 457-460 (1999), hereby incorporated by reference. By way of illustration, for the equivalent circuit depicted in FIG. 4, it is assumed that $C_s$, $R_0$, $L_0$ are equivalent characteristics of a preferred resonator in a vacuum, $C_p$ is the equivalent parallel capacitance, $\rho$ is the liquid density, $\eta$ is liquid viscosity, $\omega$ is oscillation frequency.

Accordingly, it can be seen that viscosity and density can be de-convoluted by the following "deconvolution formulae":

$Z(\omega) = Ai\omega\rho + B\sqrt{\omega\rho\eta}(1+i)$ $Z(\omega) = i\omega\Delta L + \Delta Z\sqrt{\Omega}(1+i)$ $\Delta L = A\rho, \Delta Z = B\sqrt{\rho\eta}$ The above is not intended as limiting of the present invention. Other alternative models might be derived with reference to publications such as "Frequency response of cantilever beams immersed in viscous fluids with applications to the atomic force microscope", J. E. Sader, J. Appl. Phys. 84, 64-76 (1998); "Resonance response of scanning force microscopy cantilever", G. Y. Chen, R. J. Warmack, T. Thundat, and D. P. Allison, Rev. Sci. Instrum. 65, 2532-2537(1994); and "Lecture notes on shear and friction force detection with quartz tuning forks" Work presented at the "Ecole Thématique du CNRS" on near-field optics, March 2000, La Londe les Maures, France by Khaled Karrai, Center for NanoScience, Section Physik der Ludwig-Maximilians-Universität München D-80539 München, Germany, the teachings of which are hereby incorporated by reference.

Further, it will also be appreciated that the above protocol need not be performed in every instance. For example, where the specifics of the resonator geometry and electronics are accurately known, a reduced set of measurements, such as the frequency and amplitude of the resonance peak and minimum could suffice to determine particular liquid properties. In this case, simplified detector electronics and analysis methods advantageously might be employed to facilitate incorporation in a system for on-line or real time fluid condition monitoring, which is also contemplated herein.

The sensors in accordance with the present invention advantageously provide excellent performance characteristics. Without limitation, for example, the sensors herein require less than 5V AC of excitation voltage, and on the order of less than 1 micro-amp current (e.g., about 0.1 micro-amps). Accurate measurements are obtainable in less than one second, and often less than about 0.25 seconds. The measurement range for viscosity is from about 0 to at least about 20 cPs (and possibly as high as at least about 5000 cPs) at 1g/cm$^3$. The measurement range for density is from about 0 to at least about 20 g/cm$^3$ at 1 cP. Dielectric constants are measurable over at least the range of about 1 to about 100. Resolution (density, viscosity) values of less than 1 % are also possible.

As addressed elsewhere, it should be appreciated that the sensors and other devices described herein are not intended strictly for use in environment control systems, but may be employed in other systems as well, such as machine fluid sensing systems (e.g., an oil condition sensor), a microbalance, in a flow detection system, in a petroleum exploration, drilling or processing system, or other applications.

EXAMPLES

Example 1

Referring to FIG. 5, there is shown a specific schematic illustration of one type of general system 300 in which the present invention might be employed. The system generally includes a circulation loop (e.g., a closed loop or open loop, not shown), which includes at least one conduit 302 in which a thermal change fluid is introduced as a liquid or condensable gas (e.g., via an initial charge prior to sealing the system, by a thermal change fluid reservoir or other source 304, or otherwise) that is connected to the loop via one or more suitable ports. Associated with the conduit (whether contained therein, in series therewith, in a parallel branch or otherwise), is one or more of a temperature measurement device, a pressure measurement device, a mass flow meter, or other optional condition monitoring device 306. Also associated with the line (whether separate from or integrated with the condition monitoring device 306 (e.g., as part of a manifold unit), upstream therefrom, downstream therefrom, in series with the conduit, in a parallel branch or otherwise), is one or more of the sensor 308 of the present invention, adapted for exposure to the thermal change fluid for monitoring a change in condition of the fluid. The sensor 308 is in signaling communication with a suitable signal source, and suitable data acquisition monitoring instrumentation.

Thus, in the present example, a tuning fork resonator sensor that is smaller than about 10 mm is placed in a system (using a potted two-wire connector) that includes one or a combination of refrigerant (e.g., R-134A refrigerant), a lubricant (e.g., an ester lubricant) or both. In the embodiment shown, an optional transfer manifold 310 is employed for housing the condition monitoring device 306 in combination with the tuning fork sensor. The tuning fork sensor is in signaling communication (e.g., via a 50 ohm cable) with a Hewlett Packard network analyzer, which is employed to vary the frequency of a variable frequency input signal over a predetermined frequency range and which obtains a frequency-dependent resonator response of the mechanical resonator (e.g., via a high impedance probe), and outputs the response. Results are recorded in a computer via a suitable GPIB interface and may be transferred as desired to a suitable server or other storage unit for subsequent storage.

FIG. 6 illustrates results obtainable using an approximately 3×8 mm silver coated ceramic tuning fork sensor. As can be seen sensor response is stable and a clear differentiation is observed as between the gas phase and the liquid phase, whether the liquid is a refrigerant, a lubricant, or a combination thereof, it being particularly noted that the refrigerant and lubricant combination is comfortably with the optimal sensitivity for the sensor. It should be noted that effective measurements are obtainable at different concentrations of lubricant, it being observable on the basis of experimentation in which a small chamber is constructed to receive lubricant and refrigerant combinations delivered via syringe dispensing, with refrigerant being cooled into liquid state by dry ice.

Example 2

Figure 7:
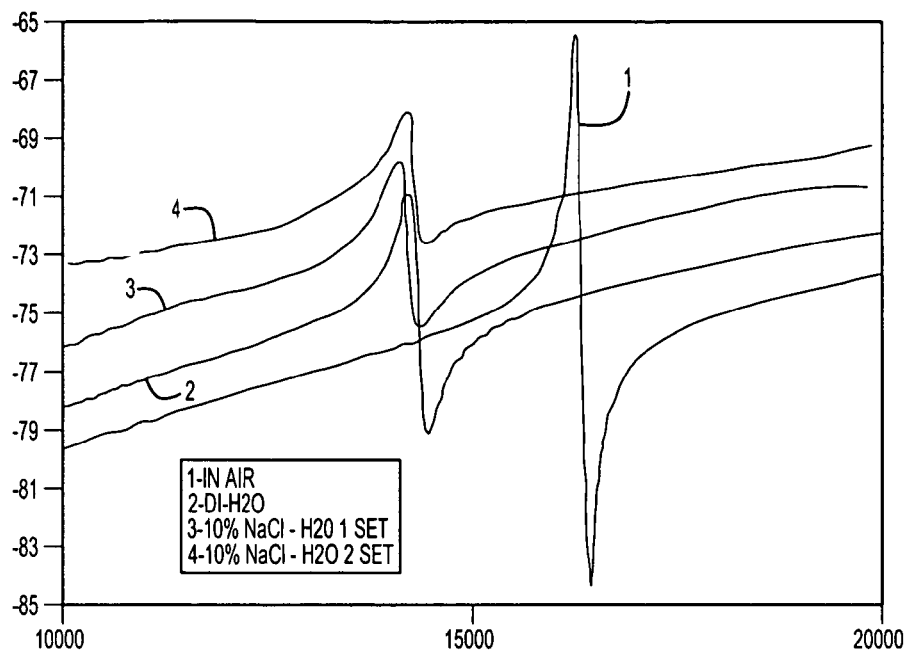

The setup of Example 1 is employed, with a resin coated (e.g., enamel) lithium niobate tuning fork sensor substituted for the tuning fork sensor of Example 1. Reproducibility across a range of different fluids is shown in FIG. 7. It will be noted from FIG. 7, that the sensors generally of the present invention is suitable for use in aqueous and saline media.

Example 3

Figure 8:
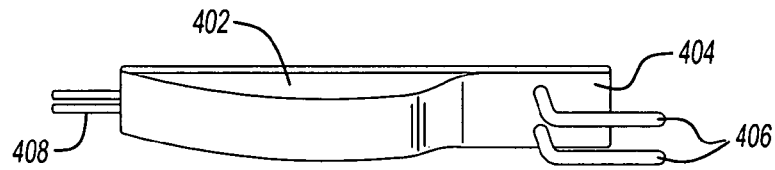
FIGS. 8 and 9 illustrate examples of sensor construction in accordance with the present invention.
Figure 9:
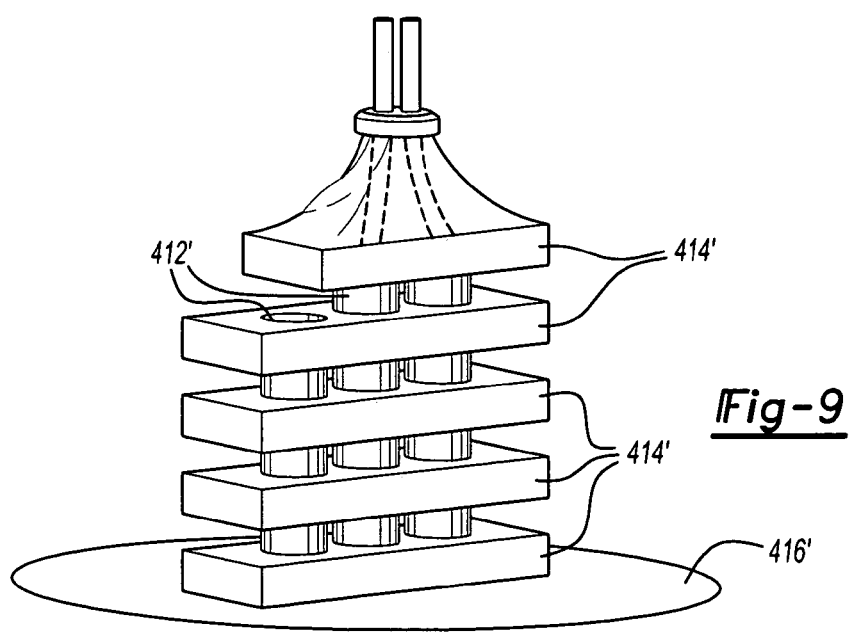

The setup of Example 1 is employed, using each of the sensors of Example 1 and Example 2, The sensor 400 (400') is coated with a coating 402 (402'). For example, the coating may include a stove enamel (e.g., an acrylic enamel), which is coated by plural brief (e.g., about 0.5 sec) spray passes, with intermediate drying (e.g., by hot air, such as above 80 C). The base portion 404 (404') and the leads 406 (406') of the sensor are optionally further coated with a resin (particularly epoxy resin) to help avoid electrical coupling with a conductive fluid to be monitored. The tuning fork in its entirety, the sensor in which it is incorporated, the tuning fork tines 408 (408'), optionally the base of the sensor, or combinations thereof are coated with a stove enamel (e.g., an acrylic enamel), such as by plural brief (e.g., about 0.5 sec) spray passes, with intermediate drying (e.g., by hot air, such as above 80 C). FIG. 8 illustrates a sensor like that of Example 1, and FIG. 9 illustrates a sensor like that of Example 2. It will be noted that the sensor of FIG. 9 may include one or more internal passages 410' such as for permitting isolation of electrical contacts. For example, conduits 412' (the number of which may be selected as desired) might be aligned relative to each other by one or a plurality of common manifolds 414' that are spaced relative to each other as shown, in contact with each other or both. The sensor may have a further resin coating between the manifolds and the conduits, at the base of the sensor or elsewhere. For example, FIG. 9 illustrates a resin coating 416' adjacent the base portion of the sensor. The resin may function as an adhesive, a protective coating or both.

Figure 10:
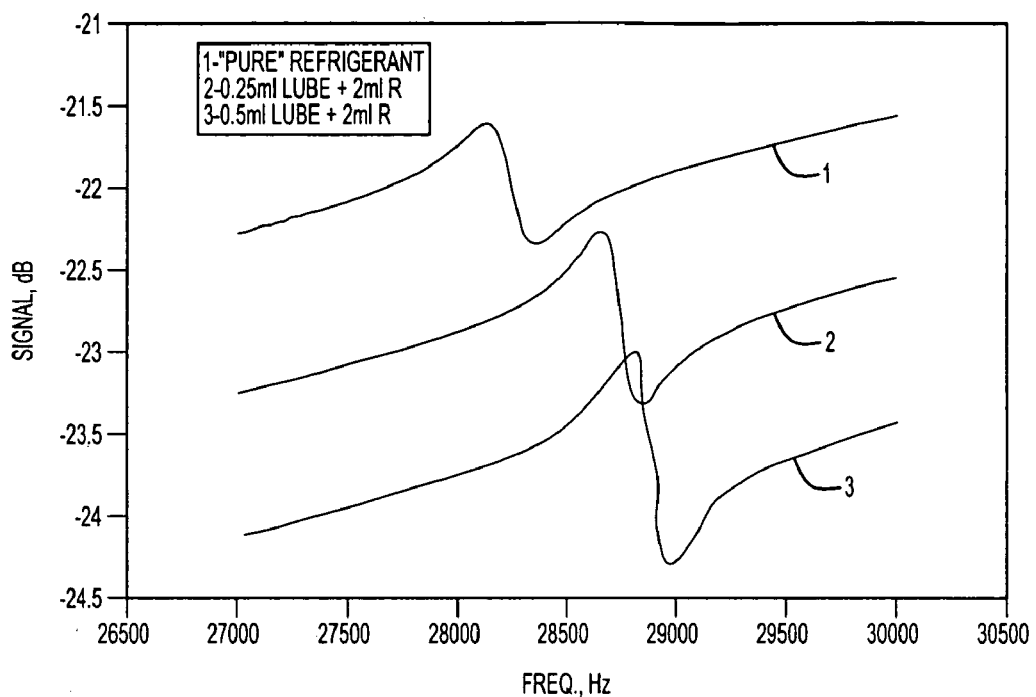
FIGS. 10 and 11 illustrate additional examples of data obtainable using the present invention.
Figure 11:
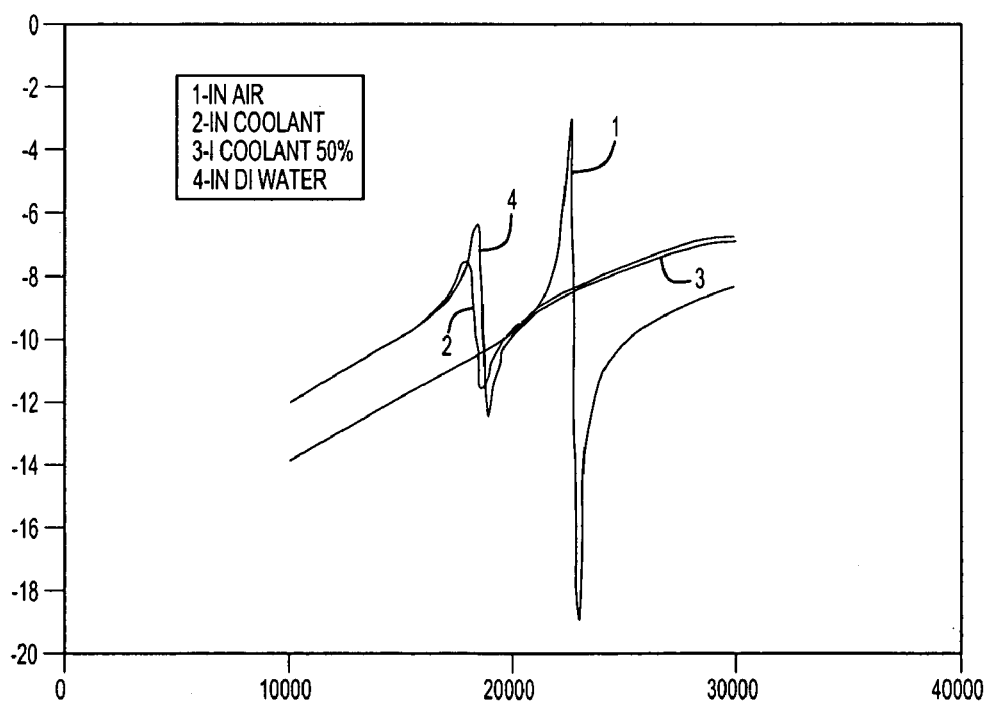

FIG. 10 illustrates exemplary results from the employment of the sensor of FIG. 8 in the monitoring of pure refrigerant (noted as "R"), refrigerant and lubricant. Successful measurements are possible in both classes of fluids. Likewise, as seen in FIG. 11 (representative of results from other resonators of the present invention as well), successful measurements are obtainable using the present invention to measure a conductive fluid such as a coolant (e.g., a glycol such as ethylene glycol).

Example 4

Figure 12A:
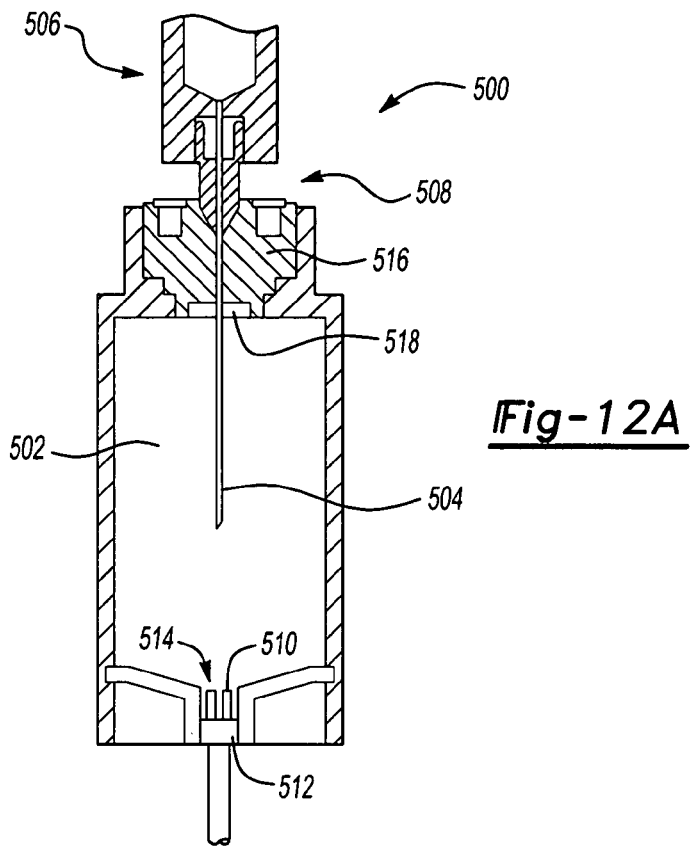
FIG. 12A illustrates an example of a fixture for use in the present invention.
Figure 12B:
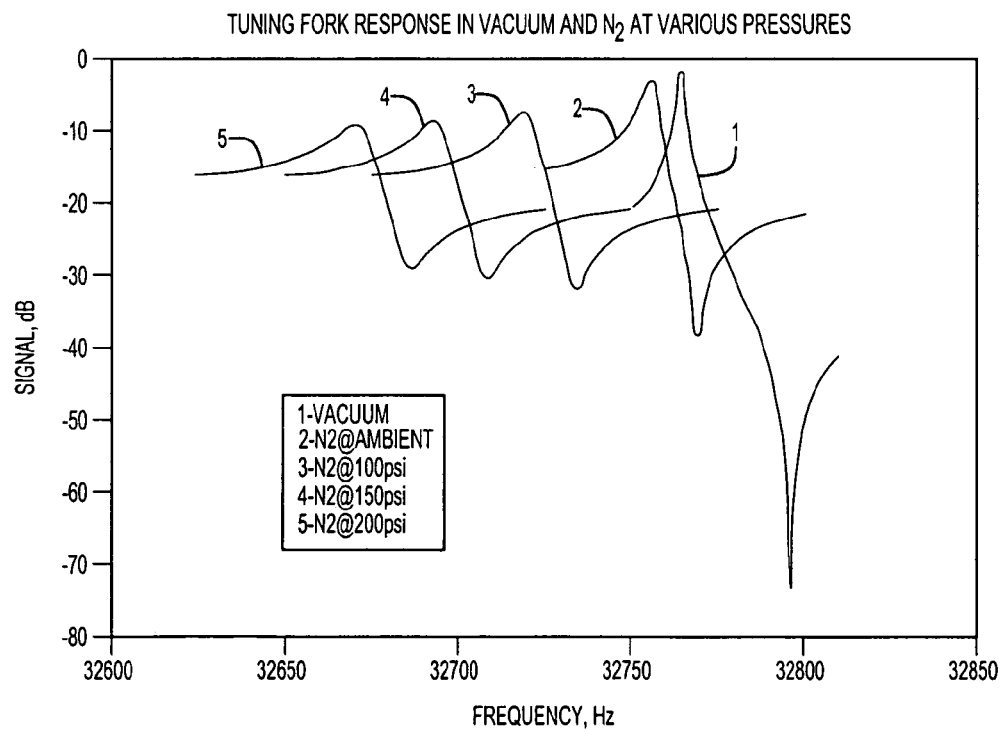
FIGS. 12B illustrates data that can be produced using the fixture of FIG. 12A.

Sensors in accordance with the present invention are used in a fixture 500, such as the illustrative example depicted in FIGS. 12A-12B. As seen in FIG. 12A, generally the fixture 500 includes a fluid chamber 502 (e.g., having a volume less than 100 ml, such as 20 ml) into which a thermal change fluid, thermal change fluid in the gas state, or other gas (e.g., air, nitrogen, or otherwise) is introduced with a fluid dispenser (e.g., via a syringe needle or other capillary, such as a 23 gage needle "RN" 504), a valve, or a combination thereof, associated with an inlet portion 506. The inlet portion 506 (which may be a permanent or removable adapter for receiving the needle 504) is optionally connected with the chamber by way of a septum 508 portion. The sensor (e.g., including a tuning fork 510) may be removably attached to the fixture via a fitting 512, such as by use of a threaded fitting, an interference fitting, a magnetic fitting, adhesive (e.g., an epoxy or otherwise), a combination thereof, or the like. Suitable electrical connections, such as described previously may be coupled with the sensor, of course, for signaling communication with an input signal, monitoring device or both. The sensor may alternatively, or additionally employ an electromagnetic wireless device for achieving signaling communication with other components. The sensor (e.g., including a tuning fork) may be positioned so that it is exposed directly to the thermal change fluid, and optionally may be located in a relatively low turbulence region, (e.g., in a well 514, within a cage, at least partially surrounded by a protective wall, or a combination thereof). The septum portion may be any suitable structure and may include, for example, a septum fitting 516 (e.g., a nut), and a seal 518 (e.g., an elastomeric seal such as a fluorocarbon elastomeric Merlin Microseal® formed or placed in the fitting). The fixture might also be suitable configured for housing a condition monitoring device such as one or both of a temperature or pressure measurement device, as well as including one or more suitable ports for fluid drainage. The FIG. 12B illustrates examples of data obtained using such fixture, where a tuning fork having the following approximate characteristics is employed:

| Tuning Fork | Size $l$ | $f^{res.}$ | $\lambda$ | $a^{res}(1V^{RMS})$ | $\delta$ | Re ~ |
|---|---|---|---|---|---|---|
| | ~2 mm | 32 KHz | 10 mm | ~30 nm | 11.4 $\mu$m | 0.9 |

To illustrate the sensitivity of the sensor to the gas phase of the refrigerant, having pressurized nitrogen in the head space as noted in FIG. 12B, the following viscosity data is observed (in cPs(0 C.101kPa)): air—1.708E-03; carbon dioxide—1.390E-03; helium—1.860E-03; hydrogen—8.345E-04; methane—1.026E-03; nitrogen—1.660E-03; and oxygen—1.919E-03. The above, of course, takes into account the values for air at ambient of the speed of sound of about 330 m/s, a density of about 1.3 kg/m³, and a viscosity of about 1.708E-03 cPs, and applies the correlations of:

$$\rho = \frac{1}{\mu}\frac{P}{RT}$$

$$\eta = \frac{1}{3\sqrt{2}\sigma}\sqrt{\frac{8mkT}{\pi}}, \sigma = \pi d^2$$

Thus, it can be seen that this system affords the ability to measure independently the pressure and the temperature in one or more particular points of the gas flow for a known gas or to discriminate between different gases by the molecular weight or compressibility parameters if a mixture of gases is present and the temperature or pressure is known.

As with all of the graphically depicted data herein, though illustrated with reference to measurements using a particular type of resonator (e.g., a tuning fork resonator), with a particular type of fluid (e.g., nitrogen fluid), like results are possible using the alternative resonators of the present invention, different fluids, or a combination thereof. For example, it is contemplated that one specific data output of the present invention will exhibit an upwardly sloping generally sinusoidal wave configuration, with a signal peak exhibited at a frequency between 10 kHz and 30 kHz. It should be appreciated, however, that the traces provided in the figures herein are not intended to limit the geometry of any resulting data outputted, and that other shapes of traces may be produced and fall within the scope of the present invention.

In short, the above examples demonstrate how sensors of the present invention can measure properties of thermal change fluids of a variety of different types.

It will be further appreciated that functions or structures of a plurality of components or steps may be combined into a single component or step, or the functions or structures of one step or component may be split among plural steps or components. The present invention contemplates all of these combinations. Unless stated otherwise, dimensions and geometries of the various structures depicted herein are not intended to be restrictive of the invention, and other dimensions or geometries are possible. Plural structural components or steps can be provided by a single integrated structure or step. Alternatively, a single integrated structure or step might be divided into separate plural components or steps. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A method for monitoring a thermal change fluid in an environmental control system, the method comprising
operating a mechanical resonator in an environmental control system selected from heating, ventilation, air conditioning and refrigeration systems, the environmental control system including a passage for a thermal change fluid, the mechanical resonator being a flexural resonator, a torsional resonator or a combination thereof,
translating at least a portion of the resonator through the thermal change fluid, the thermal change fluid comprising R-134A refrigerant, a mineral oil, an ester lubricant or a mixture thereof, and
monitoring the response of the resonator to the thermal change fluid in the passage.

2. A method for monitoring a superheat condition of a refrigerant in an environmental control system, the method comprising
superheating a refrigerant in an environmental control system, and
monitoring the superheated refrigerant with a mechanical resonator.

3. The method of claim 2 wherein the refrigerant further comprises refrigerant lubricant.

4. A method for monitoring a fluid in an environmental control system, the method comprising
pressurizing and heating a reduced pressure vapor in an environmental control system to form an elevated pressure, elevated temperature vapor,
condensing the elevated pressure, elevated temperature vapor to form an elevated pressure liquid,
expanding the elevated pressure liquid to form a reduced pressure liquid,
evaporating the reduced pressure liquid to form a reduced pressure vapor, and
monitoring a fluid selected from one or more of the elevated pressure, elevated temperature vapor, the elevated pressure liquid, the reduced pressure liquid, the reduced pressure vapor and combinations thereof, the fluid being monitored with a mechanical resonator.

5. The method of claim 4 wherein the fluid includes a liquid, gas, or combination thereof, selected from refrigerants, refrigerant lubricants, coolants, or combinations of two or more of such fluids.

6. The method of claim 4 wherein the fluid comprises R-134A refrigerant, a mineral oil, an ester lubricant or a mixture thereof.

7. The method of claims 1, 2 or 4 wherein the resonator is coated over at least a portion of its outer surface.

8. The method of claims 1, 2 or 4 wherein the resonator comprises a resonator element made of a piezoelectric material.

9. The method of claims 1, 2 or 4 wherein the resonator comprises a resonator element made of lithium niobate.

10. The method of claims 2 or 4 wherein the mechanical resonator is a flexural resonator, a torsional resonator or a combination thereof.

11. The method of claims 1, 2 or 4 wherein the resonator is selected from tuning forks, cantilevers, unimorphs, bimorphs, membrane resonators, torsion bars or combinations thereof.

12. The method of claims 1, 2 or 4 wherein the resonator is a tuning fork resonator.

13. The method of claims 1, 2 or 4 wherein the resonator is a piezoelectric tuning fork resonator.

14. The method of claims 1, 2 or 4 wherein the resonator is operated at frequencies of less than about 1 MHz.

15. The method of claims 1, 2 or 4 further comprising the step of employing data obtained from the monitoring step to perform at least one operation of the environmental control system or a component thereof.

16. The method of claim 15 wherein the at least one operation of the environmental control system is selected from switching the environmental control system or one or more components therein to an on or off state, closing or opening a valve in the environmental control system, changing a flow rate of the thermal change fluid or refrigerant, changing a pressure of the thermal change fluid or refrigerant, changing the operating speed or condition of one or more components of the environmental control system, providing a visual output signal, providing an audible output signal, or a combination thereof.

17. The method of claims 1, 2 or 4 wherein the monitoring step comprises monitoring at least one of fluid viscosity, fluid density, fluid conductivity, fluid viscosity/density product, or fluid dielectric constant.

18. The method of claim 1, 2 or 4 wherein the monitoring step further comprises a step selected from monitoring a change of frequency of the resonator while maintaining an input signal to the resonator as a constant, monitoring the change in electrical feedback from the resonator while maintaining the input signal to the resonator as a constant, varying the frequency of a variable frequency input signal over a predetermined frequency range to obtain a frequency-dependent resonator response of the resonator, comparing the response of the resonator with a prior response of the resonator, comparing the response of the resonator with a known reference value for the thermal change fluid, comparing the response of the resonator with the response of another resonator in the system, or a combination of two or more such steps.

19. The method of claims 2 or 4 wherein the environmental control system is an air conditioning or refrigeration system.

20. An environmental control system selected from heating, ventilation, air conditioning and refrigeration systems, the system comprising
   a passage containing a thermal change fluid, the thermal change fluid comprising R-134A refrigerant, a mineral oil, an ester lubricant or a mixture thereof,
   at least one mechanical resonator for relative translation with the thermal change fluid, the mechanical resonator being a flexural resonator, a torsional resonator or a combination thereof, and
   a circuit for monitoring a response of the resonator to the thermal change fluid.

21. The system of claim 20 wherein the thermal change fluid includes a liquid, gas, or combination thereof.

22. The system of claim 20 wherein the environmental control system comprises an electronic component environmental control system.

23. The system of claim 20 wherein the environmental control system comprises a motor used to drive a compressor, and the thermal change fluid comprises a fluid used in the compressor motor.

24. The system of claim 20 further comprising a source of an input signal in signaling communication with the resonator, the input signal resulting from an electrical impulse, a mechanical impulse or combinations thereof.

25. The system of claim 24 wherein the input signal is an electrical signal selected from a variable frequency input signal; a constant frequency input signal; a voltage spike, a sine wave burst or combinations thereof.

26. A superheat monitoring system for use in an environmental control system comprising a refrigerant, the system comprising
   at least one mechanical resonator for contacting a superheated refrigerant in the environmental control system, and
   a circuit for monitoring a response of the resonator to the superheated refrigerant, the monitoring circuit comprising a processing unit adapted to receive a signal from the resonator, the processing unit being programmed with an algorithm for monitoring the superheat condition of a fluid in the system.

27. The system of claim 26 wherein the monitoring circuit further comprises an amplifier for amplifying the signal from the resonator for receipt by the processing unit.

28. The system of claim 26 wherein the system further comprises a temperature measurement device, and the processing unit is in signaling communication with the temperature measurement device.

29. An environmental control system, comprising
   a compressor for compressing a reduced pressure vapor to form an elevated pressure, elevated temperature vapor,
   a condenser for removing heat from and condensing the elevated pressure, elevated temperature vapor to form an elevated pressure liquid,
   an expansion device for reducing the pressure of the elevated pressure liquid to form a reduced pressure liquid,
   an evaporator for evaporating the reduced pressure liquid to form the reduced pressure vapor,
   at least one passage for containing a refrigerant, the refrigerant comprising a fluid selected from one or more of the elevated pressure, elevated temperature vapor, the elevated pressure liquid, the reduced pressure liquid, the reduced pressure vapor, and combinations thereof,
   a mechanical resonator positioned to contact the refrigerant in the passage, and
   a circuit for monitoring the response of the resonator to the refrigerant in the passage.

30. The system of claims 26 or 29, wherein the refrigerant further comprises refrigerant lubricant.

31. The system of claims 20, 26 or 29 wherein the resonator is coated over at least a portion of its outer surface.

32. The system of claims 20, 26 or 29 wherein the resonator comprises a resonator element made of a piezoelectric material.

33. The system of claims 20, 26 or 29 wherein the resonator comprises a resonator element made of lithium niobate.

34. The system of claims 26 or 29 wherein the mechanical resonator is a flexural resonator, a torsional resonator or a combination thereof.

35. The system of claims 20, 26 or 29 wherein the resonator is selected from tuning forks, cantilevers, unimorphs, bimorphs, membrane resonators, torsion bars or combinations thereof.

36. The system of claims 20, 26 or 29 wherein the resonator is a tuning fork resonator.

37. The system of claims 20, 26 or 29 wherein the resonator is a piezoelectric tuning fork resonator.

38. The system of claims 20, 26 or 29 wherein the resonator is operated at frequencies of less than about 1 MHz.

39. The system of claims 26 or 29 wherein the environmental control system is an air conditioning or refrigeration system.

40. The system of claims 20, 26 or 29 wherein the environmental control system comprises a passenger comfort system of a transportation vehicle.

41. The system of claims 20 or 29 wherein the monitoring circuit further comprises a processing unit adapted to receive a signal from the resonator.

42. The system of claim 41 wherein the monitoring circuit further comprises an amplifier for amplifying the signal from the resonator for receipt by the processing unit.

43. The system of claim 41 wherein the system further comprises a temperature measurement device, and the processing unit is in signaling communication with the temperature measurement device.

* * * * *